US005939253A

United States Patent [19]
Scholl et al.

[11] Patent Number: 5,939,253
[45] Date of Patent: Aug. 17, 1999

[54] COMPOSITIONS AND METHODS FOR DETECTING VIRAL INFECTION

[75] Inventors: David R. Scholl; Joseph D. Jollick, both of Athens, Ohio

[73] Assignee: Diagnostic Hybrids, Inc., Athens, Ohio

[21] Appl. No.: 08/638,323

[22] Filed: Apr. 26, 1996

[51] Int. Cl.[6] .............................. C12Q 1/70; C12Q 1/68
[52] U.S. Cl. ................................... 435/5; 435/6
[58] Field of Search ................... 435/5, 8, 69.1, 435/69.8, 70.1, 172.3, 235.1, 240.2, 320.1, 6; 536/23.72, 24.1

[56] References Cited

U.S. PATENT DOCUMENTS 5,418,132  5/1995  Olivo ........................................... 435/5

OTHER PUBLICATIONS

Astier–Gin et al. (1995) "Identification of HTLV–I– or HTLV–II–producing cells by cocultivation with BHK–21 cells stably transfected with a LTR–lacZ gene construct," J. Virological Methods 51:19–30.
Schmidt et al. (1989) In "Diagnostic Procedures for Viral, Rickettsial and Chlamydial Infections," 6th Edition, Eds. Schmidt et al., pp. 1–35.
Schmidt (1989) In "Diagnostic Procedures for Viral, Rickettsial and Chlamydial Infections," 6th Edition, Eds. Schmidt et al., pp. 51–100.
Hierholzer (1989) In "Diagnostic Procedures for Viral, Rickettsialal and Chlamydial Infections," 6th Edition, Eds. Schmidt et al., pp. 241–248.
Ashley et al. (1989) In "Diagnostic Procedures for Viral, Rickettsial and Chlamydial Infections," 6th Edition, Eds. Schmidt et al., pp. 293–299.
Stagno et al. (1989) In "Diagnostic Procedures for Viral, Rickettsial and Chlamydial Infections," 6th Edition, Eds. Schmidt et al., pp. 338–342.
Waner et al. (1989) In "Diagnostic Procedures for Viral, Rickettsial and Chlamydial Infections," 6th Edition, Eds. Schmidt et al., pp. 386–397.
Nakano et al. (1989) In "Diagnostic Procedures for Viral, Rickettsial and Chlamydial Infections," 6th Edition, Eds. Schmidt et al., pp. 489–491.
Grandien et al. (1989) In "Diagnostic Procedures for Viral, Rickettsial and Chlamydial Infections," 6th Edition, Eds. Schmidt et al., pp. 525–534, and 541–542.
Gwaltney et al. (1989) In "Diagnostic Procedures for Viral, Rickettsial and Chlamydial Infections," 6th Edition, Eds. Schmidt et al., pp. 596–599, and 601–603.
Schieble (1989) In "Diagnostic Procedures for Viral, Rickettsial and Chlamydial Infections," 6th Edition, Eds. Schmidt et al., pp. 621–626.
Harmon et al. (1989) In "Diagnostic Procedures for Viral, Rickettsial and Chlamydial Infections," 6th Edition, Eds. Schmidt et al., pp. 644 and 650–654.
Mufson (1989) In "Diagnostic Procedures for Viral, Rickettsial and Chlamydial Infections," 6th Edition, Eds. Schmidt et al., pp. 674 and 679–682.
Walsh et al. (1989) In "Diagnostic Procedures for Viral, Rickettsial and Chlamydial Infections," 6th Edition, Eds. Schmidt et al., pp. 699 and 703–705.
Fuccillo et al. (1989) In "Diagnostic Procedures for Viral, Rickettsial and Chlamydial Infections," 6th Edition, Eds. Schmidt et al., pp. 722–723.
Best et al. (1989) In "Diagnostic Procedures for Viral, Rickettsial and Chlamydial Infections," 6th Edition, Eds. Schmidt et al., pp. 747 and 750–753.
Jahrling (1989) In "Diagnostic Procedures for Viral, Rickettsial and Chlamydial Infections," 6th Edition, Eds. Schmidt et al., p. 871.
Johnson (1989) In "Diagnostic Procedures for Viral, Rickettsial and Chlamydial Infections," 6th Edition, Eds. Schmidt et al., p. 911.
Herrmann et al. (1989) In "Diagnostic Procedures for Viral, Rickettsial and Chlamydial Infections," 6th Edition, Eds. Schmidt et al., p. 938.
Purcell et al. (1989) In "Diagnostic Procedures for Viral, Rickettsial and Chlamydial Infections," 6th Edition, Eds. Schmidt et al., p. 973.
Ascher et al. (1989) In "Diagnostic Procedures for Viral, Rickettsial and Chlamydial Infections," 6th Edition, Eds. Schmidt et al., pp. 1115–1116 and 1119–1123.
Sureau (1993) "In vitro culture systems for hepatitis B and delta viruses," Arch. Virol. Suppl. 8:3–14.
Chemicon Catalogue (1992) "Immunologic Reagents for Research And Diagnostics," pp. 6–11.
Diagnostic Procedures for Viral, Rickettsial and Chlamydial Infections, 6th Edition, Eds. Schmidt et al., Table of Contents.
Spector (1989) In "Diagnostic Procedures for Viral, Rickettsial and Chlamydial Infections," 6th Edition, Eds. Schmidt et al., pp. 203–218.
Gleaves et al. (1992) "Detection of Human Cytomegovirus in Clinic Specimens by Centrifugation Culture with a Non-human Cell Line," J. Clin. Microbiol. 30(4):1045–1048.
Ausubel et al., *Current Protocols in Molecular Biology* (1987) John Wiley & Sons, Inc., 16.17.9.
QIAGEN products catalogue obtained from the Internet at http://www.qiagen.com/products/dna4.html and http://www.qiagen.com/products/q974dna1.html, and http://www.qiagen.com/products/q975rnal.

(List continued on next page.)

*Primary Examiner*—Nancy Degen
*Assistant Examiner*—Robert Schwartzman
*Attorney, Agent, or Firm*—Medlen & Carroll, LLP

[57] ABSTRACT

The present invention generally relates to the field of diagnostic virology. More particularly, the present invention is directed to methods and compositions useful for the detection and differentiation of viral particles and/or virions in specimens. The present invention also provides methods and compositions useful for evaluating the susceptibility of infectious viruses to antiviral agents.

25 Claims, 16 Drawing Sheets

OTHER PUBLICATIONS

Martin et al. (1991) J. Virol. 65(10):5381–5390.

Stabell et al. (1992) "Isolation of a cell line for rapid and sensitive histochemical assay for the detection of herpes simplex virus," J. Virol. Methods 38:195–204.

*Virology,* Fields and Knipe, Eds., Raven Press, pp. 1795–2062.

McGeoch et al., *Nucleic Acids Res.,* 14:1727–1745 (1986).

McGeoch et al., *J. Gen. Virol,* 69:1531–1574 (1988).

Baer et al., *Nature,* 310:207–211 (1984).

Davidson and Scott, *J Gen Virol,* 67:1759–1816 (1986).

Nikas et al., *Proteins: Structure, Function, and Genetics,* 1:376–384 (1986).

Kowalski, R.P. and Gordon, Y.J., *Opthal.,* 96:1583–1586 (1989).

Gleaves et al., *J. Clin. Mircro.,* 21:29–32 (1985).

Ziegler et al., *J. Clin. Micro.,* 26:2013–2017 (1985).

Puchhammer–Stockl et al., *J. Med. Virol.,* 32:77–82 (1990).

Rocancourt et al., *J. Virol.,* 64:2660–2668 (1990).

Kimpton, J. and Emerman, M., J. Virol., 66:4:2232–2239 (1992).

Mosca, J.D., et al., *Nature,* 325:67–70 (1987).

Mosca, J.D., et al., *Proc. Natl. Acad. Sci,* 84:7408–7412 (1987).

Popik and Pitha, *Proc. Natl. Acad. Sci.,* 88:9572–9577 (1981).

Stabell et al., *J. Clin. Microbiol.,* 31:2796–2798 (1993).

Maniatis et al., Science, 236:1237 (1987).

Voss et al., Trends Biochem. Sci., 11:287 (1986).

Dijkema et al., EMBO J., 4:761 (1985).

Uetsuki et al., J. Biol. Chem., 264:5791 (1989).

Kim et al., Gene, 91:217 (1990).

Mizushima and Nagata, Nuc. Acids. Res., 18:5322 (1990).

Gorman et al., Proc. Natl. Acad. Sci. USA, 79:6777 (1982).

Boshart et al., Cell, 41:521 (1985)

Sambrook et al., Molecular Cloning: A Laboratory Manual, 2nd ed., Cold Spring Harbor Laboratory Pres, New York, pp. 16.7–16.8 (1989).

Sambrook, supra, at 16.6–16.7.

Wymer et al., *J. Virol.,* 63:2773–2784 (1989).

Bean, B., *Clin. Microbiol. Rev.* 5:146–182 (1992).

Ausubel et al., *Current Protocols in Molecular Biology,* John Wiley & Sons, Inc., Unit 9.4 (1987).

Goldstein and Weller, *J. Virol.,* 62:196–205 (1988).

Saiki, R.K. et al., *Science,* 239:487–491 (1988).

Maniatis, T., et al. (*Molecular Cloning: A Laboratory Manual,* Cold Spring Harbor Laboratory (1990).

Stabell et al. "Isolation of a cell line for rapid and sensitive histochemical assay for the detection of herpes simplex virus," *J. Vir. Meth.,* 38:195–204 (1992).

Wick, "Transgenic Technology Makes Diagnostic Virology Accessible," *Genetic Engineering News* 15: (1995).

Chang et al. "Human Immunodeficiency Viruses Containing Heterologous Enhancer/Promoters Are Replication Competent and Exhibit Different Lymphocyte Tropisms," *J. Vir.,* 67:743–752 (1993).

Akagi et al. "Murine retroviral vectors expressing the tax1 gene of human T–cell leukemia virus type 1," *Gene* 106:255–259 (1991).

Schindler et al., "Investigation of ELVIS Technology for use in HSV Typing of Clinical Specimens," Abstract, 11th Annual Clinical Virology Symposium, May 1, 1995, Clearwater Beach, FL.

Jollick et al., "Typing of HSV with the ELVIS HSV typing system: different staining characteristics do not result from promoter–transactivator specificity," Abstract, 12th Annual Clinical Virology Symposium, Clearwater FL (1996).

1. M.W. MARKERS
2. HSV-1 DNA TEMPLATE, *pol* PRIMERS
3. HSV-1 DNA TEMPLATE, ICP10 PROMOTER PRIMERS
4. HSV-2 DNA TEMPLATE, *pol* PRIMERS
5. HSV-2 DNA TEMPLATE, ICP10 PROMOTER PRIMERS

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

GTCATGCCAG ACAACAGC

18

(2) INFORMATION FOR SEQ ID NO:2:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

CCGACAGGAA CGCAACAGG

19

COMPOSITIONS AND METHODS FOR DETECTING VIRAL INFECTION

FIELD OF THE INVENTION

This invention generally relates to the field of diagnostic virology and, more particularly, to methods for detecting and differentiating as to viral type in a specimen, and to evaluating the susceptibility of a virus to an antiviral agent and a mixture of cell lines for use therefor.

BACKGROUND OF THE INVENTION

Herpesviruses have been found in most animal species and approximately 100 herpesviruses have been at least partially characterized. These include species causing diseases in humans, horses, cattle, pigs, and chickens. In humans, the seven herpesviruses that have been thus far isolated are viewed as important causes of human morbidity and mortality. [Whitley, R. J., *Virology* (1990) New York, Raven Press]. Thus, the availability of methods for detecting infectious herpesviruses has become increasingly important.

The eight known human herpesviruses are herpes simplex virus type 1 (HSV-1), herpes simplex virus type 2 (HSV-2), human cytomegalovirus (HCMV), varicella-zoster virus (VZV), Epstein-Barr virus (EBV), human herpes virus 6 (HHV6), human herpes virus 7 (HHV7), and herpes human virus 8. The herpesviruses differ with respect to the diseases they cause. HSV-1 infection produces skin vesicles or mucosal ulcers generally limited to the oropharynx; HSV-2 produces mucocutaneous lesions generally in the genital region; HCMV can infect monocytes and a number of organ systems including salivary glands, kidneys, liver and lung; VZV causes the diseases of chickenpox and shingles; EBV infects the oropharyngeal epithelium and B lymphocytes; and HHV6, HHV7 and HHV8 infect mononuclear cells and, in children, produce skin eruptions (Roseola Infantum). (*Virology*, Fields and Knipe, Eds., Raven Press, pp. 1795–2062).

The human herpesviruses HSV-2, HHV6 and HHV7 have been partially sequenced and HSV-1, HCMV, EBV and VZV have been completely sequenced. (McGeoch et al., *Nucleic Acids Res.* 14:1727–1745, 1986 and McGeoch et al., *J. Gen. Virol* 69:1531–1574, 1988; Chee et al., *DNA Seq.* 2:1–12, 1991; Baer et al., *Nature* 310:207–211, 1984; Davidson and Scott, *J Gen Virol* 67:1759–1816, 1986). Furthermore, the DNAs of the human herpesviruses have been found to be similar, but not identical. For example, all known human herpesviruses have DNA sequences that encode a ribonucleotide reductase enzyme, which contains a large subunit referred to as Infected-Cell Protein (ICP). In HSV-1 this DNA sequence encodes a ribonucleotide reductase large subunit (ICP6) that has 38% homology at the N-terminal portion and 93% homology at the C-terminal portion of the corresponding HSV-2 protein (ICP10). (Nikas et al., *Proteins: Structure, Function, and Genetics* 1:376–384, 1986). The corresponding ribonucleotide reductase large subunit in VZV shows between 43% and 53% homology beginning at HSV-1 amino acid 384 and VZV amino acid 16. Id.

Herpes simplex viruses Types 1 and 2 (hereinafter referred to collectively as HSV) infect a large number of individuals each year. Primary infection of immunocompetent patients with HSV usually leads to a mucocutaneous syndrome such as herpes labialis (HSV-1) or herpes genitalis (HSV-2), the latter being one of the most common sexually transmitted diseases today. Infection with HSV can also cause more serious infections, the most serious of which are sight-threatening keratitis and life-threatening encephalitis. Moreover, HSV related disease in immunocompromised individuals such as newborns, leukemia patients, organ transplant recipients and AIDS patients has become an increasingly prevalent and difficult problem.

Significant advances have been made in the treatment of HSV infections in the past decade. These advances in antiviral therapy have expanded the role of the diagnostic virology laboratory and have identified the need for more sensitive, accurate and rapid diagnostic tests to assist in the early diagnosis of HSV infections.

Various tests are presently available for the diagnosis of HSV infections. Most involve the detection of viral antigens or intact infectious virus. Antigen detection assays offer the advantage of rapidity and specificity, but lack the necessary sensitivity. [Kowalski, R. P. and Gordon, Y. J., *Opthal.* (1989) 96:1583–1586]. The most reliable test to detect infectious herpesvirus involves inoculation of specimens onto tissue culture cells followed by detection of infectious virus by microscopically observing a characteristic cytopathic effect.

Although HSV is a relatively easy virus to culture as it replicates on a wide variety of continuous cell lines, virus propagation in tissue culture can be slow and expensive. Recently, improved techniques have been developed for the detection of viruses from clinical specimens. The shell vial technique, for instance, has greatly increased the sensitivity and the rapidity of HSV detection. When this method is combined with antigen detection by immunohistochemistry, HSV can be positively identified within 24 hours in the majority of cases. Gleaves et al., *J Clin. Mircro.* (1985) 21:29–32; Ziegler et al., *J. Clin. Micro.* (1985) 26:2013–2017. While this type of assay is preferred in diagnostic virology applications, it is labor intensive and a significant number of specimens are not identified as positive until after 48 hours.

Another recent technological advance, polymerase chain reaction (PCR) technology, presents a promising tool for the detection of HSV particularly in cerebrospinal fluid specimens, but this technology detects viral nucleic acid and not infectious virus. (Puchhammer-Stockl, et al., *J. Med. Virol.* (1990) 32:77–82). The detection of infectious virus is preferred because it definitively indicates that there is an ongoing viral infection with active viral replication. PCR detection of viral nucleic acid may only be indicative of the presence of a remnant of a past infection or the presence of a latent infection.

The commercial availability of HSV type-specific monoclonal antibodies has enhanced the ability of the diagnostic virology practice to provide a result which identifies HSV-1 (majority of oral infections) or HSV-2 (majority of genital infections) from a clinical specimen. However, the 48 hour procedure is time consuming, expensive and labor intensive in that it requires duplicate cultures be inoculated with clinical specimen. After 24–48 hours, one culture is reacted with antibody to HSV-1 antigen and the duplicate culture is reacted with antibody to HSV-2 antigen. After multiple steps and incubation periods, the two cell cultures are evaluated microscopically to determine which of the two antibody reagents produced a positive detection signal on the infected cell monolayer.

Previous scientific studies involving herpesviruses have used susceptible cell lines transfected with a chimeric DNA construct containing a marker gene in transient assays to study various aspects of the virus such as the regulation of gene expression during viral replication. [Flanagan W. M. and Wagner, K. K., *Virus Genes* 1:1:61–71 (1987)]. These studies have not, however, described a DNA construct stably integrated into the chromosome of a stable cultured cell line which is suitable for the diagnostic detection and quantification of a herpesvirus in a specimen with the requisite sensitivity and specificity for a clinical diagnostic assay.

A method for detecting infectious HIV in a specimen has been disclosed that utilizes a genetically engineered cell line containing a chimeric gene having the *E. coli* lacZ gene associated with the HIV-1 LTR promoter. [Rocancourt, et al., *J. Virol.* (1990) 64:2660–2668; Kimpton, J. and Emerman, M., *J. Virol.* (1992) 66:4:2232–2239]. Although these cell lines may be useful for detecting HIV in a specimen, they are not suitable for diagnostic virology assays because of their lack of specificity. It is well-known that the HIV-1 LTR promoter used in the DNA construct of these studies to cause expression of the reporter gene is not specific for HIV and that other viruses cause expression of the reporter gene if present in the specimen. In particular, the presence of HSV or cytomegalovirus in the specimen causes activation of the LTR promoter and subsequent expression of the reporter gene even in the absence of HIV in a specimen. [Mosca, J. D., et al., *Nature* (1987) 325:67 70; Mosca, J. D., et al., *Proc. Natl. Acad. Sci.* (1987) 84:7408–7412; Popik and Pitha, *Proc. Natl. Acad. Sci.* (1981) 88:9572–9577]. If such a cell line were used in a diagnostic assay, it could lead to the erroneous diagnosis of the presence of HIV in a specimen when in fact the specimen contained a different virus. Thus, the lack of specificity in cell lines prepared to detect HIV in a specimen prevents their use in a diagnostic assay which requires specificity.

Recently, a method for detecting infectious HSV in a specimen has been disclosed that utilizes a genetically engineered cell line containing a chimeric gene having the *E. coli* lacZ gene associated with the HSV-1 promoter region for the viral ribonucleotide reductase, known as ICP6 [U.S. Pat. No. 5,418,132 to Olivio, herein incorporated by reference and Stabell et al., *J. Clin. Microbiol.* 31:2796–2798 (1993)]. When either HSV-1 or HSV-2 infects this line, β-galactosidase (the product of the lacZ gene) is made and accumulates in the cytoplasm of induced cells. While this genetically engineered cell line allows for the detection of infectious HSV in a sample, it cannot distinguish between the HSV-1 and HSV-2 types.

A need exists, therefore, for methods of detecting infectious virus, including herpesvirus, in a specimen that provides rapid detection in a cost efficient manner, while also providing the sensitivity and specificity necessary for a diagnostic assay. Ideally, the diagnostic assay would allow the identification of different types of virus (e.g., HSV-1 and HSV-2).

SUMMARY OF THE INVENTION

In one embodiment, there is provided a novel assay for detecting the presence of an infectious herpesvirus in a specimen. The assay provides an enzymatic means for identifying the presence of a herpesvirus that can be visually observed or easily detected. The assay involves inoculating a DNA-transfected cell line with a specimen suspected of containing a herpesvirus, allowing a sufficient period of time for the herpesvirus infectious cycle to proceed, and detecting and quantifying the number of herpesvirus-infected cells to determine the number of infectious herpesvirus virions in the specimen. The cell line used in the assay is genetically engineered to express a reporter gene only if infectious herpesvirus is present in the specimen. The assay also reliably quantifies the number of herpesvirus in a specimen and is so sensitive that it is capable of detecting the presence of a single virion in a specimen.

In another embodiment, the invention provides a novel cell line for use in the assay. The cell line is a DNA-transfected cell line susceptible to infection by a herpesvirus which is stably transformed with a chimeric gene comprising a herpesvirus inducible promoter and a gene coding for an enzyme, the expression of the enzyme being dependent upon and quantitatively proportional to the presence of herpesvirus. In one preferred embodiment, the cell line is a stable baby hamster kidney cell line the genome of which has been engineered to contain the *E. coli* lacZ gene behind (3' to) an inducible HSV promoter, the HSV-1 ICP6 promoter or the HSV-2 ICP10 promoter. In a second preferred embodiment, the lacZ gene is replaced with the gene encoding firefly luciferase.

In a further embodiment, the invention provides a kit for assaying the presence of an infectious herpesvirus in a specimen. The kit includes a supply of DNA transfected cells susceptible to infection by the desired herpesvirus being assayed for and engineered to contain a reporter gene, which codes for an enzyme that can be easily detected, behind an inducible herpesvirus promoter, and the reagents necessary to detect expression of the enzyme.

In another embodiment, there is provided novel mixed cell line compositions. Monolayer mixtures comprised of genetically engineered cell lines and non-engineered permissive cell lines in a range of ratios. In a preferred embodiment the genetically engineered cell line component of the mixed cell bed is a stable baby hamster kidney cell line the genome of which has been engineered to contain the *E. coli* LacZ gene behind (3' to) an inducible HSV promoter, the HSV-1 ICP6 promoter or the HSV-2ICP10 promoter combined with the non-engineered, HSV-1 and HSV-2 permissive cell line, human embryonic lung cell (MRC-5), (available from the ATCC and the Medical Research Council in England) in a mixed cell monolayer at a ratio of 10:90.

In still another embodiment, the invention provides novel compositions comprised of cell lines from human and non-human origin, with one serving to act as a permissive cell line which permits HSV to proliferate throughout the monolayer and the other to have the virus passed to it and thereby effectively signal the presence of virus through specific viral induction of its reporter gene.

In yet another embodiment, the invention provides a method for assaying the degree of inhibition of HSV-1 and HSV-2 by putative antiviral agents investigated for potential efficacy. In a preferred embodiment mixed cell lines comprised of a majority of permissive cells and a minority of reporter cells susceptible to the virus of interest are prepared in multi-well plates. After the mixed cell monolayers have obtained confluence, a viral sample capable of being adsorb onto the mixed cell monolayers would be inoculated into a number of cell-containing wells and allowed to adsorb to the mixed cells. Appropriate maintenance medium is then applied which contains an antiviral drug of interest at various concentrations to which the viral isolate is to be tested for susceptibility. Maintenance medium without drug serves as a no drug control to monitor uninhibited viral proliferation. After a sufficient period of time for viral proliferation to spread virus to reporter cells in the no drug monolayer, all samples are fixed and stained or alternatively lysed and analyzed, for either histochemical analyses or colorimetric, fluorometric, or luminometric analyses, respectively.

Among the several advantages of the present invention may be noted the provision of a rapid and sensitive assay for detecting the presence of an infectious herpesvirus in a clinical specimen that is suitable as a diagnostic assay; the provision of such an assay that differentiates HSV-1 and HSV-2 types; the provision of such an assay that provides reliable results in a single test; the provision of such an assay which can determine the inhibitory effect of antiviral compounds against HSV; the provision of such an assay that is adaptable to an automated format; the provision of such an assay that is adaptable for use as an automated assay; the provision of such an assay that is capable of detecting the proliferative effects from a single infectious virion; and the provision of compositions of mixed cell lines for use in such assays that expresses a reporter gene only after infection with the specific herpesvirus(es) of interest.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

BRIEF DESCRIPTION OF THE INVENTION

Figure 1:
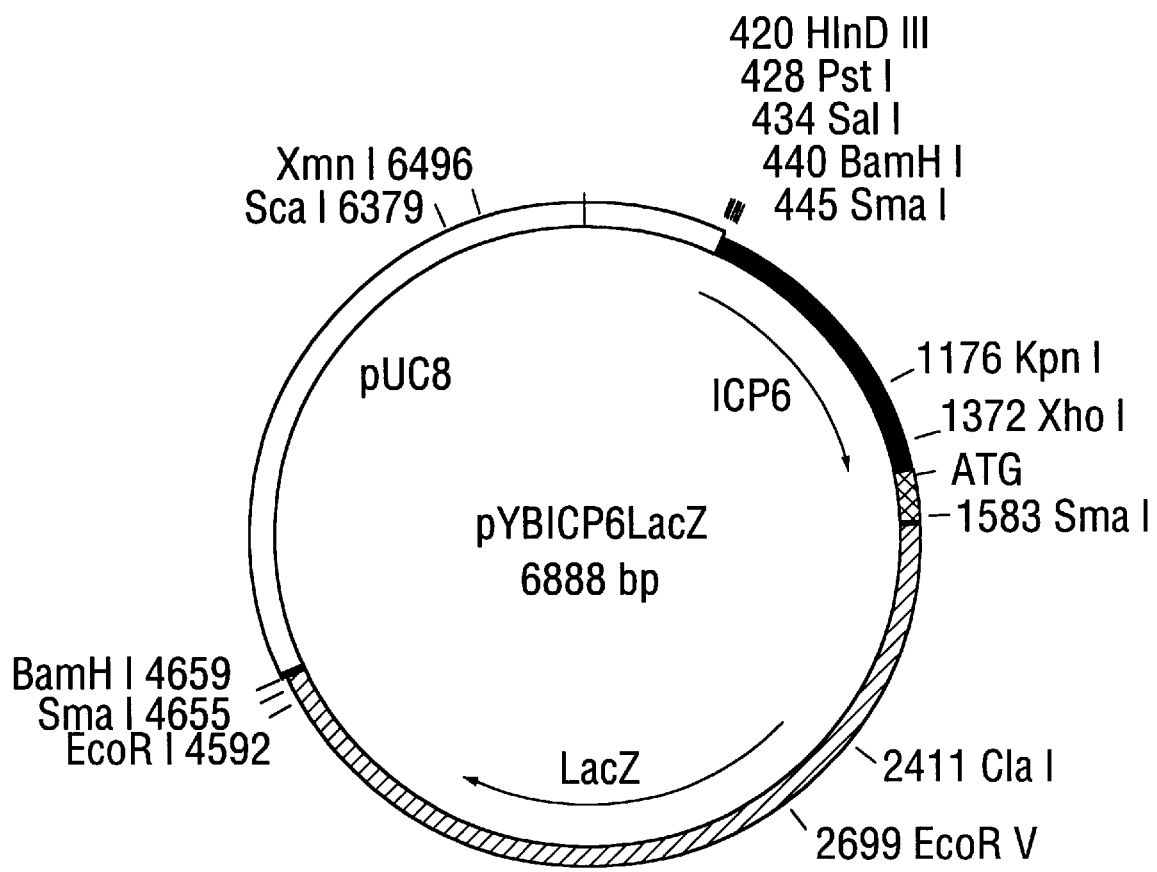
FIG. 1 is a schematic representation of pYBICP6LacZ.

This invention generally relates to the field of diagnostic virology and, more particularly, to methods for detecting and differentiating virus(es) present in specimens, and evaluating the susceptibility of a viruses to antiviral agents.

In one embodiment, the present invention provides methods for the detection of infectious virus in a specimen comprising the steps of: a) providing a specimen suspected of containing a virus, a cell line permissive for infection by the virus, and a genetically engineered cell line containing an oligonucleotide having a sequence comprising a promoter sequence derived from the virus, wherein the promoter sequence is operably linked to a reporter gene, and wherein the expression of the reporter gene is dependent upon and quantitatively proportional to the presence of the virus; b) mixing together the permissive cell line and the genetically engineered cell line to create a mixed cell culture; c) inoculating the mixed cell culture with the specimen under conditions which permit the infection of the mixed cell culture by the virus; and d) detecting the expression of the reporter gene and thereby detecting the presence of virus in the specimen. In one preferred embodiment, the mixed cell culture is a mixture consisting of 80–99% of the permissive cell line and 1–20% of the genetically engineered cell line.

In a preferred embodiment of the method, the promoter sequence contains a promoter derived from a gene selected from the group comprising genes that encode ribonucleotide reductase and genes that encode one or more subunits of ribonucleotide reductase. In a particularly preferred embodiment, the promoter sequence is derived from a gene that encodes a large subunit of a ribonucleotide reductase and the virus is a member of the herpesvirus family. It is not intended that the present invention be limited to a specific promoter sequence. Indeed, in one alternative embodiment, the promoter sequence is the ICP10 promoter and the herpesvirus is Herpes Simplex Virus Type 2 (HSV-2). In another alternative embodiment, the promoter sequence is the ICP6 promoter and the herpesvirus is Herpes Simplex Virus Type 1 (HSV-1). However, other promoter sequences and other herpesviruses are also contemplated. It is contemplated that the herpesvirus will be selected from the group comprising HSV-1, HSV-2, Human Cytomegalovirus (CMV), Varicella-Zoster Virus (VZV), Epstein-Barr Virus (EBV), Human Herpes Virus 6 (HHV-6), Human Herpes Virus 7 (HHV-7), and Human Herpes Virus 8 (HHV-8), although it is not intended that the present invention be limited to any of the listed herpesviruses. Indeed, it is contemplated that any member of the herpesvirus family may be detected in the present invention, including but not limited to herpesviruses that infect humans.

In one embodiment of the method, the genetically engineered cell line contains an oligonucleotide having a sequence comprising a herpesvirus inducible promoter operably linked to a reporter gene selected from the group comprising the *Escherichia coli* lacZ gene and a luciferase gene. In one preferred embodiment of the method, the genetically engineered cell line is BHKICP10LacZ. In an alternative preferred embodiment, the genetically engineered cell line is BHKICP6LacZ. However, it is not intended that the reporter gene be limited to the lacZ and luciferase genes. Indeed, it is contemplated that any suitable reporter gene known to those in the art will be useful in the method of the present invention.

It is also contemplated that various permissive cell lines will be useful in the method of the present invention. In one embodiment, the permissive cell line is permissive for infection with herpesvirus. In a particularly preferred embodiment, the permissive cell line is MRC-5.

It is contemplated that the method of the present invention will be used in conjunction with controls of known positivity and negativity for the virus(es) of interest. Thus, it is contemplated that the pattern of reporter gene expression present in a test sample (e.g., from a clinical specimen) will be compared to the patterns of reporter gene expression in control samples known to be positive and/or negative for the virus(es) of interest. It is also contemplated that effects unrelated to the expression of the reporter gene will be detectable, including but not limited to CPE. These effects, alone and in combination with the reporter gene expression may be used to detect the presence of viral infection.

The present invention also provides methods for the typing of infectious herpesvirus in specimens, comprising the steps of: a) providing a specimen suspected of containing one or more members of the herpesvirus family, a cell line permissive for infection by one or more members of the herpesvirus family, a genetically engineered cell line containing an oligonucleotide having a sequence comprising a promoter sequence derived from a member of the herpesvirus family wherein the promoter sequence is operably linked to a reporter gene, and the expression of the reporter gene is dependent upon and quantitatively proportional to the presence of herpesvirus and wherein the expression of the reporter gene varies in a distinguishable manner as a result of the presence of different members of the herpesvirus family; b) mixing together the permissive cell line and the genetically engineered cell line to create a mixed cell culture; c) inoculating this mixed cell culture with the specimen under conditions which permit the infection of the mixed cell culture by members of the herpesvirus family, wherein the infection results in a distinguishable pattern of expression by the reporter gene; d) detecting the expression of the reporter gene and thereby detecting the presence of one or more members of the herpesvirus family in the specimen; and e) identifying the presence of a specific member of the herpesvirus family based upon the resulting distinguishable pattern. It is contemplated that this pattern of expression will be observable by various assisted and non-assisted methods, including visual observation by eye, spectrophotometric observation, etc. It is not intended that the detection of distinguishable pattern(s) be limited to any particular method of detection.

In a preferred embodiment of the typing method of the present invention, the mixed cell culture is a mixture consisting of 80–99% of the permissive cell line and 1–20% of the genetically engineered cell line. As with the first method described, it is not intended that the present invention be limited to any particular herpesvirus. In one particular embodiment, the member of the herpesvirus family detected and typed using the method of the present invention is selected from the group comprising HSV-1, HSV-2, CMV, VZV, EBV, HHV-6, HHV-7, and HHV-8. It is intended that one or more herpesviruses may be detected and typed in one specimen. In this manner, co-infection with multiple herpesviruses may be diagnosed. For example, it is contemplated that mixed infections with HSV-1 and HSV-2 may be detectable and the infections distinguished using the methods of the present invention.

In one embodiment of the typing method, the reporter gene comprises *Escherichia coli* lacZ gene. However, it is not intended that the reporter gene be limited to lacZ. Indeed, it is contemplated that any reporter gene may be used in this method. In one particularly preferred embodiment, the detection of the reporter gene is accomplished through the use of histochemical staining. It is contemplated that one member of the herpesvirus family will produce an histochemically pattern of expression that is distinguishable from the histochemical patterns produced by other members of the herpesvirus family. In this manner, it is possible to use the methods of the present invention to distinguish infection with one herpesvirus from infection with another herpesvirus.

It is contemplated that the method of the present invention will be used in conjunction with controls of known positivity and negativity for the virus(es) of interest. Thus, it is contemplated that the pattern of expression present in a test sample (e.g., from a clinical specimen) will be compared to the patterns of expression in control samples known to be positive and/or negative for the virus(es) of interest. It is also contemplated that effects unrelated to the expression of the reporter gene will be detectable, including but not limited to CPE. These effects, alone and in combination with reporter gene expression may be used to detect the presence of viral infection, as well as provide information to distinguish between viruses.

In yet another embodiment, the present invention provides a composition comprising a mixed cell culture, wherein the mixed cell culture comprises the combination of a genetically engineered cell line transformed with a promoter sequence from a virus, wherein the promoter sequence is operably linked to a reporter gene, and wherein expression of the reporter gene is dependent upon and quantitatively proportional to the presence of virus, and a non-engineered cell line which is permissive for virus infection.

In one embodiment of the composition, the mixed cell culture is a mixture consisting of 1–20% of the genetically engineered cell line and 80–99% of the permissive cell line. In one preferred embodiment of the composition, the genetically engineered cell line component may comprise a promoter for a gene that encodes ribonucleotide reductase. In an alternative preferred embodiment, the promoter may comprise genes that encode one or more subunits of ribonucleotide reductase. In one particularly preferred embodiment, the genetically engineered cell line is BHKICP10LacZ, while in another particularly preferred embodiment, the genetically engineered cell line is BHKICP6LacZ. In an alternative embodiment of the composition, the genetically engineered cell line comprises an *E. coli* lacZ gene positioned 3' to a virus inducible promoter. It is contemplated that this lacZ gene be positioned immediately 3' to this virus-inducible promoter. However, it is not intended that these sequences will be contiguous. Indeed, it is contemplated only that the reporter and promoter genes are operably linked. Furthermore, it is contemplated that the composition will comprise promoter sequences from any virus, including but not limited to members of the herpesvirus family. It is also contemplated that the non-engineered cell line be permissive for infection by any number of viruses, including but not limited to members of the herpesvirus family.

In one preferred embodiment, the composition includes a genetically engineered cell line which includes a promoter for a gene that encodes a ribonucleotide reductase large subunit and the virus is a member of the herpesvirus family selected from the group consisting of HSV-1, HSV-2, CMV, VZV, EBV, HHV-6, HHV-7, and HHV-8. However, it is not intended that the present invention be limited to any particular herpesvirus. In one preferred embodiment, the genetically engineered cell line component contains an ICP10 promoter and the herpesvirus family member is HSV-2, while in another preferred embodiment, the genetically engineered cell line comprises an ICP6 promoter and the herpesvirus family member is HSV-1.

It is contemplated that the detection of reporter gene expression be accomplished through the use of various methods, including, but not limited to colorimetric, fluorimetric or luminometric assays or assay systems. In one preferred embodiment, the reporter gene encodes β-galactosidase.

In one embodiment, the composition includes a genetically engineered cell line that is a mammalian cell line susceptible to infection by virus. In one preferred embodiment, the genetically engineered cell line comprises baby hamster kidney cells (e.g., cell lines derived from BHK cells). In one embodiment, the composition includes a permissive cell line that is permissive to infection by herpesviruses, including but not limited to HSV-1 and HSV-2. In a particularly preferred embodiment, the permissive cell line is MRC-5. It is not intended that the composition of the present invention be limited to detection of viral infection based on the expression of the reporter gene, as effects such as CPE may also be detectable.

The present invention also provides a kit for assaying for the presence of infectious herpesvirus in a specimen. The kit includes: a) a supply of a mixed cell line comprised of a cell line of genetically engineered mammalian cells susceptible to infection by herpesvirus, wherein the cell line contains an oligonucleotide having a sequence comprising a virus promoter sequence operably linked to a reporter gene, and where the expression of the reporter gene is dependent upon and quantitatively proportional to the presence of virus in the specimen; and a cell line permissive for virus; and b) a supply of reagents to detect the expression of the reporter gene. It is not intended that the promoter sequences present within the genetically engineered cell line be limited to any particular virus or virus family. It is contemplated that any virus promoter will be useful in the kit of the present invention. However, in one preferred embodiment, herpesvirus promoter sequences are present in the genetically engineered cell line.

It is contemplated that various promoter sequences will be useful in the kit of the present invention. However, in a preferred embodiment, the promoter encodes either a complete ribonucleotide reductase enzyme, or in the alternative, subunits of ribonucleotide reductase. In one particularly preferred embodiment, the promoter sequence contains a promoter for a gene that encodes a ribonucleotide reductase large subunit and the herpesvirus is a herpesvirus family member selected from the group consisting of HSV-1, HSV-2, CMV, VZV, EBV, HHV-6, HHV-7, and HHV-8. However, it is not intended that the kit will be limited to this list of herpesviruses. Indeed, it is contemplated that any herpesvirus may be detected using the present kit. In one particularly preferred embodiment of the kit, the promoter sequence contains an ICP10 promoter and the herpesvirus family member is HSV-2, while in an alternative preferred embodiment, the promoter sequence contains an ICP6 promoter and the herpesvirus family member is HSV-1.

In one preferred embodiment of the kit, the promoter sequence present in the genetically engineered cell line comprises an E. coli lacZ gene that is operably linked to a herpesvirus inducible promoter. In one particularly preferred embodiment, the genetically engineered mammalian cells are BHKICP10LacZ cells, while in an alternative embodiment, the cells are BHKICP6LacZ cells.

In one preferred embodiment, the reporter gene encodes β-galactosidase. However, it is not intended that the present invention be limited to any particular reporter gene. It is also contemplated that the reporter gene will encode any number of enzymes that are amenable to detection by various methods, including but not limited to such methods as colorimetric, fluorimetric or luminometric assay systems. In one preferred embodiment of the kit, the reagents provided for the detection of reporter gene expression may include, but are not limited to, solutions of 5-bromo-4-chloro-3 indolyl-β-D-galactopyranoside, o-nitrophenyl-galactopyranoside solution, and fluorescein di-β-D-galactopyranoside. However, it is not intended to limit the kit to these assay systems, as other systems (e.g., radiometric assay systems) may be useful.

It is contemplated that the kit of the present invention may also include additional components, such as materials suitable for positive and negative controls and instructions for use. It is not intended that the kit of the present invention be limited to the mixed cell line and reagents for the detection of reporter gene expression. It is also intended that the kit will be useful for detection of viral effects on cells other than and unrelated to reporter gene expression. For example, it is contemplated that the kit may be useful for detection of CPE.

DEFINITIONS

To facilitate understanding of the invention, a number of terms are defined below.

The term "recombinant DNA molecule" as used herein refers to a DNA molecule which is comprised of segments of DNA joined together by means of molecular biological techniques.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotides is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements which direct transcription of a linked gene are generally located 5' or upstream of the coding region (enhancer elements can exert their effect even when located 3' of the promoter element and the coding region). Transcription termination and polyadenylation signals are located 3' or downstream of the coding region.

The term "an oligonucleotide having a nucleotide sequence encoding a gene" means a DNA sequence comprising the coding region of a gene or, in other words, the DNA sequence which encodes a gene product. The coding region may be present in either a cDNA or genomic DNA form. Suitable control elements such as enhancers, promoters, splice junctions, polyadenylation signals, etc. may be placed in close proximity to the coding region of the gene if needed to permit proper initiation of transcription and/or correct processing of the primary RNA transcript. Alternatively, the coding region utilized in the vectors of the present invention may contain endogenous enhancers and/or promoters, splice junctions, intervening sequences, polyadenylation signals, etc. or a combination of both endogenous and exogenous control elements.

The term "transcription unit" as used herein refers to the segment of DNA between the sites of initiation and termination of transcription and the regulatory elements necessary for the efficient initiation and termination. For example, a segment of DNA comprising an enhancer/promoter, a coding region, and a termination and polyadenylation sequence comprises a transcription unit.

The term "regulatory element" as used herein refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc. (defined infra).

The terms "reporter gene construct" or "reporter gene vector" as used herein refers to a recombinant DNA molecule containing a sequence encoding the product of a reporter gene and appropriate nucleic acid sequences necessary for the expression of the operably linked coding sequence in a particular host organism. Eukaryotic cells are known to utilize promoters, enhancers, and termination and polyadenylation signals.

The term "reporter gene" refers to an oligonucleotide having a sequence encoding a gene product (typically an enzyme) which is easily and quantifiably assayed when a construct comprising the reporter gene sequence operably linked to a heterologous promoter and/or enhancer element is introduced into cells containing (or which can be made to contain) the factors necessary for the activation of the promoter and/or enhancer elements. Examples of reporter genes include but are not limited to bacterial genes encoding β-galactosidase (lacZ), the bacterial chloramphenicol acteyltransferase (cat) genes, firefly luciferase genes and genes encoding β-glucuronidase (GUS).

Transcriptional control signals in eukaryotes comprise "promoter" and "enhancer" elements. Promoters and enhancers consist of short arrays of DNA sequences that interact specifically with cellular proteins involved in transcription [Maniatis, et al., Science 236:1237 (1987)]. Promoter and enhancer elements have been isolated from a variety of eukaryotic sources including genes in yeast, insect and mammalian cells and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are finctional in a limited subset of cell types [for review see Voss, et al., Trends Biochem. Sci., 11:287 (1986) and Maniatis, et al., supra (1987)]. For example, the SV40 early gene enhancer is very active in a wide variety of cell types from many mammalian species and has been widely used for the expression of proteins in mammalian cells [Dijkema, et al, EMBO J. 4:761 (1985)]. Two other examples of promoter/enhancer elements active in a broad range of mammalian cell types are those from the human elongation factor 1α gene [Uetsuki et al., J. Biol. Chem., 264:5791 (1989); Kim et al., Gene 91:217 (1990); and Mizushima and Nagata, Nuc. Acids. Res., 18:5322 (1990)] and the long terminal repeats of the Rous sarcoma virus [Gorman et al., Proc. Natl. Acad. Sci. USA 79:6777 (1982)] and the human cytomegalovirus [Boshart et al., Cell 41:521 (1985)].

The term "promoter/enhancer" denotes a segment of DNA which contains sequences capable of providing both promoter and enhancer functions (for example, the long terminal repeats of retroviruses contain both promoter and enhancer functions). The enhancer/promoter may be "endogenous" or "exogenous" or "heterologous." An endogenous enhancer/promoter is one which is naturally linked with a given gene in the genome. An exogenous (heterologous) enhancer/promoter is one which is placed in juxtaposition to a gene by means of genetic manipulation (i.e., molecular biological techniques).

The presence of "splicing signals" on an expression vector often results in higher levels of expression of the recombinant transcript. Splicing signals mediate the removal of introns from the primary RNA transcript and consist of a splice donor and acceptor site [Sambrook et al., Molecular Cloning: A Laboratory Manual, 2nd ed., Cold Spring Harbor Laboratory Press, New York (1989) pp. 16.7–16.8]. A commonly used splice donor and acceptor site is the splice junction from the 16S RNA of SV40.

Efficient expression of recombinant DNA sequences in eukaryotic cells requires signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one which is isolated from one gene and placed 3' of another gene. A commonly used heterologous poly A signal is the SV40 poly A signal. The SV40 poly A signal is contained on a 237 bp BamH/BclI restriction fragment and directs both termination and polyadenylation [Sambrook, supra, at 16.6–16.7]. This 237 bp fragment is contained within a 671 bp BamHI/PstI restriction fragment.

The term "genetically engineered cell line" refers to a cell line that contains heterologous DNA introduced into the cell line by means of molecular biological techniques (i.e., recombinant DNA technology).

The term "stable transfection" or "stably transfected" refers to the introduction and integration of foreign DNA into the genome of the transfected cell. The term "stable transfectant" refers to a cell which has stably integrated foreign DNA into the genomic DNA.

The term "selectable marker" as used herein refers to the use of a gene which encodes an enzymatic activity that confers resistance to an antibiotic or drug upon the cell in which the selectable marker is expressed. Selectable markers may be "dominant"; a dominant selectable marker encodes an enzymatic activity which can be detected in any mammalian cell line. Examples of dominant selectable markers include the bacterial aminoglycoside 3' phosphotransferase gene (also referred to as the neo gene) which confers resistance to the drug G418 in mammalian cells, the bacterial hygromycin G phosphotransferase (hyg) gene which confers resistance to the antibiotic hygromycin and the bacterial xanthine-guanine phosphoribosyl transferase gene (also referred to as the gpt gene) which confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene which is used in conjunction with tk cell lines, the CAD gene which is used in conjunction with CAD-deficient cells and the mammalian hypoxanthine-guanine phosphoribosyl transferase (hprt)

gene which is used in conjunction with hprt⁻ cell lines. A review of the use of selectable markers in mammalian cell lines is provided in Sambrook et al., supra at pp. 16.9–16.15

The terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The abbreviation "BHK" refers to baby hamster kidney cells; the BHK cell line is available from the ATCC (ATCC CRL No. 6281).

The terms "confluent" or "confluency" as used herein in reference to an adherent cell line defme a condition wherein cells throughout a culture are in contact with each other creating what appears to be a continuous sheet or "monolayer" of cells.

The terms "cytopathic effect" or "CPE" as used herein describe changes in cellular structure (i.e. a pathologic effect) resulting from external agents such viruses. Common cytopathic effects include cell destruction, syncytia (i.e. fused giant cells) formation, cell rounding vacuole formation, and formation of inclusion bodies. CPE results from actions of a virus on permissive cells that negatively affect the ability of the permissive cellular host to preform its required functions to remain viable. In in vitro cell culture systems, CPE is evident when cells, as part of a confluent monolayer, show regions of non-confluence after contact with a specimen that contains a virus. The observed microscopic effect is generally focal in nature and the foci is initiated by a single virion. However, depending upon viral load in the sample, CPE may be observed throughout the monolayer after a sufficient period of incubation. Cells demonstrating viral induced CPE usually change morphology to a rounded shape, and over a prolonged period of time can die and be released form their anchorage points in the monolayer. When many cells reach the point of focal destruction, the area is called a viral plaque, which appears as a hole in the monolayer. Cytopathic effects are readily discernable and distinguishable by those skilled in the art.

The abbreviation "CV-1" represents a continuous cell line derived from African Green Monkey Kidney; the CV-1 cell line is available from the ATCC (ATCC CCL 70).

The term "Vero" as used herein describes another continuous cell line derived from African Green Monkey Kidney; the Vero cell line is available from the ATCC (ATCC CCL 81).

As used herein, the term "mixed cell culture" refers to a mixture of two types of cells. More specifically, the term refers to a permissive cell line and a genetically engineered cell line.

The abbreviation "ONPG" represents o-Nitrophenyl b-D-Galactopyranoside. ONPG is a substrate for the enzyme β-galactosidase (β-gal). The reaction between ONPG and β-gal produces a yellow product which can be quantified spectrophotometrically at 405 nm.

The abbreviation "X-gal" represents the chemical compound 5-bromo-4-chloro-3-indoyl-β-D-galactopyranoside, a substrate for the enzyme β-galactosidase. The reaction between X-gal and β-galactosidase results in the formation of a blue precipitate which is visually discernable.

The term "hybriwix" represents a product of Diagnostic Hybrids, Inc., Athens, Ohio which allows for quantification of certain viral DNA in an infected monolayer of cells by DNA hybridization. "DNA hybridization" is the annealing of two complimentary DNA molecules whose base sequences match according to the rules of base pairing. DNA hybridization is used to identify or quantify an unknown or "target" DNA by hybridization to a known DNA or "probe." The probe is typically labeled with a reporter molecule such as $^{125}I$, a radioisotope which can be detected and quantified with a gamma counter.

The phrase "plaque reduction assay" or "PRA" as used herein describes a standard method used to determine efficacy of anti-viral drugs by enumerating a decrease in plaque formation in a cell monolayer exposed to a drug. A "plaque" is a defined area of "CPE". It is usually the result of infection of the cell monolayer with a single infectious virus which then replicates and spreads to adjacent cells of the monolayer. A plaque may also be referred to as a "focus of viral infection".

The term "permissive" as used herein describes the sequence of interactive events between a virus and its putative host cell. The process begins with viral absorption to the host cell surface and ends with release of infectious virions. A cell is "permissive" if it readily permits the spread of virus to other cells. Many methods are available for the determination of the permissiveness of a given cell line, including, but not limited to plaque reduction assays, comparisons of the production and/or quantitation of viral proteins based on results obtained from gel electrophoresis, relative comparisons using hybridization analysis to analyze DNA or RNA content, etc.

The term "susceptible" as used herein describes the extent that a permissive or non-permissive host cell can adsorb and be penetrated by a virus. A cell line may be susceptible without being permissive in that it can be penetrated but not release virions. A permissive cell line however must be susceptible.

The phrase "seed on" as used herein describes the act of transferring an aqueous solution of suspended cells into a vessel containing cells adhered to a surface, after which the vessel is stored for a sufficient period of time to allow the suspended cells or "seeds" to settle out by gravity and attach in a relatively uniform manner to the adhered cells and become integrated into the final cell monolayer as a mixture. A "mixed cell monolayer" results from the "seed on" process.

The phrase "seed in" as used herein describes the mixing of two or more aqueous solutions of suspended tissue culture cells, each cell suspension having different cellular properties, and transfer of such mixture of cells into a vessel which is stored for a sufficient period of time to allow the suspended cells to settle out by gravity and attach in a relatively uniform manner such that the distribution of any single cell type is reflective of the relative ratio of the cells in the original mixture.

The term "starts" as used herein refers to the reporter cells which represent a primary infection of virus. The virus infects a reporter cell (a genetically engineered cell) and induces the expression of the reporter gene. A reporter cell can be nonpermissive (i.e. permissiveness of the reporter cells is not required) and still produce starts.

The phrase "viral proliferation" as used herein describes the spread or passage of infectious virus from a permissive cell type to additional cells of either a permissive or susceptible character.

The terms "specimen" or "sample" are used interchangeably in the present specification and claims and are used in their broadest sense. On the one hand they are meant to include a clinical specimen (i.e., sample) or culture (e.g., microbiological cultures). On the other hand, it is meant to include both biological and environmental samples.

Biological samples or specimens may be animal, including human, fluid, solid (e.g., stool) or tissue, as well as liquid and solid food and feed products and ingredients such as dairy items, vegetables, meat and meat by-products, and waste. Biological samples may be obtained from all of the various families of domestic animals, as well as feral or wild animals, including, but not limited to, such animals as ungulates, bear, fish, lagamorphs, rodents, etc.

Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

As used herein, the term "herpesvirus family" refers to all of the virus types included within the Herpesviridae family. Examples include HSV-1, HSV-2, VZV, B virus, equine abortion virus (EAV; equine herpesvirus 1), LK virus (equine herpesvirus 2), pseudorabies virus, infectious bovine rhinotracheitis (IBR), feline rhinotracheitis virus, Marek's disease virus, Roseolovirus, and many other viruses which infect humans as well as other animals. It is not intended that the present invention be limited to a particular member, class of viruses or herpes virus grouping (e.g., alphaherpesviruses, betaherpesviruses, and gammaherpesviruses).

As used herein, the term "distinguishable pattern" refers to the distinctive pattern of gene expression that may be detected in a test system such as a mixed cell culture. It is contemplated that infection with various viruses will result in varying patterns of expression, and thereby permit the detection and/or differentiation of the virus(es) present in a sample.

As used herein, the term "histochemical staining" refers to staining methods which are conducted directly on cells. It is contemplated that the staining be conducted in situ within cell growth chambers (e.g., flasks or roller bottles containing monolayers of cells). However, it is also contemplated that staining be conducted on cells transferred from their growth chamber to supporting structures such as microscope slides, etc.

Herpesvirus promoters may be temporally classified into three subclasses: alpha, beta and gamma. The alpha promoters mediate early viral activity (i.e., proteins involved in host penetration). The beta promoters mediate intermediate early stage viral activity (i.e., processes which establish the virus within the host cell). Finally gamma promoters are associated with late stage viral cycle activities such as replication proteins and eruption out of the host cell.

DETAILED DESCRIPTION OF INVENTION

The present invention provides methods and compositions for the detection of infectious virus in a specimen. In addition, the present invention provides methods and compositions which permit the identification (i.e., the typing) of different types of virus within a family of viruses (e.g., the Herpes Virus family) without the need to employ multiple cultures. Using the methods of the present invention, a determination of the type of virus present in a specimen can be determined using a single culture. The methods of the present invention employ mixtures of cell lines which comprise a mixture of 1) a cell line permissive for infection with a virus or a family of viruses and 2) a genetically engineered cell line which contain a reporter gene construct comprising a viral promoter sequence operably linked to a reporter gene. The viral promoter selected has the characteristic of being inactive in a cell in the absence of viral gene products (e.g., transactivators) which specifically bind to the viral promoter and induce or activate expression therefrom. These viral promoters are said to be both specific for and inducible by viral gene products expressed by the virus from which the promoter is derived. Activation of the viral promoter results in the expression of the reporter gene product, typically an enzyme, which is readily detectable in the infected cells.

The Description of the Invention is divided into the following sections: I. Cell Lines Permissive for Viral Infection, II. Genetically Engineered Cell Lines, III. Generation of Mixed Cell Cultures, IV. Infection of Mixed Cell Cultures, V. Detection of Reporter Gene Products and VI. Detection of Infectious Virus and Typing of Infectious Virus In Specimens.

I. Cell Lines Permissive For Viral Infection

The methods of the present invention employ mixed cell cultures in diagnostic assays for the detection and/or typing of infectious virus in specimens. These mixed cell cultures contain cells lines which are permissive for infection by the virus whose presence is to be detected. A cell line is said to be permissive for infection by a virus if that cell line readily permits the spread of virus from an infected cell to other cells in the culture. Permissivity describes the sequence of interactive events between a virus and its putative host cell. The process begins with viral absorption to the host cell surface and ends with release of infectious virions. Methods well known to the art allow the determination of whether any given cell line is permissive for infection by a specific virus(es). For example, the proliferation of a particular virus in a host cell line can be measured by the relative production of various viral markers (i.e., various viral gene products) over a defined period of time. Specific viral markers would include viral proteins (e.g., the gene products of the early ($\alpha$), intermediate early ($\beta$) and late ($\gamma$) genes of the herpesviruses), viral nucleic acid (including both RNA and DNA) and the progeny virus. The amount of these viral markers would increase over time following the inoculation of a permissive cell line with virus. The degree of permissivity of one cell line as compared to another cell line can be determined by quantitation of the amount of the viral markers which are produced over a given time period following inoculation of the two cultures. Suitable assays for this quantitation include the use of electrophoretic analysis (i.e., SDS-PAGE) of protein extracts prepared from the infected cell cultures to permit a comparison of the relative amounts of viral proteins produced, by the comparison of the relative amount of viral DNA or RNA produced in the two cell lines using hybridization assays or by a comparison of the relative amount of virus released into the culture medium (the culture medium or supernatants are harvested and used in a plaque titration assay to determine the amount of progeny virus produced in each cell line).

In preferred embodiments, the methods and compositions of the invention are used to detect the presence of herpesvirus and in particular for the detection of HSV. Cell lines permissive for infection with HSV include, but are not limited to human embryonic kidney (HEK) cell lines, human foreskin fibroblasts (HEF), primary rabbit kidney (PRK) cells. human embryonic lung (HEL) cells, Hep-2 cells (human epithelial carcinoma), the RD cell line (a human rhabdomyosarcoma; ATCC CCL 136); the A549 cell line (a human lung adenocarcinoma; ATCC CCL 185); mink lung (ML) cells; the Vero cell line (ATCC CCL 81); the CV-1 cell line (ATCC CCL 70); Buffalo green monkey kidney (BGMK) cells and the MRC-5 cell line (ATCC CCL 171).

II. Genetically Engineered Cell Lines

The genetically engineered cell lines of the present invention may contain the chimeric viral promoter/reporter gene sequences stably integrated into the genomic DNA of the cell. The recipient cell line used to create the genetically engineered cell line is a cell line which is susceptible for infection by the virus(es) to be detected. A susceptible cell line may be a cell line which is either permissive or non-permissive for viral infection as long as the cell line can adsorb and be penetrated by a virus. A cell line may be susceptible without being permissive in that it can be penetrated but not release virions. A permissive cell line is necessarily a susceptible cell line. The recipient cell line used to create the genetically engineered cell line may be either susceptible or permissive for infection.

Examples of suitable susceptible cell lines for herpesviruses include rabbit skin fibroblasts, baby hamster kidney cells, African green monkey cells and the like. One preferred cell line for the detection of HSV in a sample comprises baby hamster kidney cells into whose genome has been stably integrated a chimeric gene comprising the $E.\ coli$ lacZ gene behind the HSV-1 ICP6 promoter, and, in particular, a cell line identified as BHKICP6LacZ and clones thereof. Another preferred cell line for the detection of HSV in a specimen comprises baby hamster kidney cells into whose genome has been stably integrated a chimeric gene comprising the firefly luciferase gene behind the HSV-1 ICP6 promoter, and, in particular, a cell line identified as BHKICP6LucA6 and clones thereof.

Another preferred cell line for the detection of HSV in a sample comprises baby hamster kidney cells into whose genome has been stably integrated a chimeric gene comprising the $E.\ coli$ lacZ gene behind the HSV-2 ICP10 promoter, and, in particular a cell line identified as BHKICP10LacZ and clones thereof.

The methods of the present invention are not limited to the use of stably transfected cell lines as the genetically engineered cell line. Permissive cell lines which are transiently transfected with the chimeric viral promoter/reporter gene sequences may be employed. When transient transfected cell lines are to be employed, DNA comprising the chimeric viral promoter/reporter gene construct are introduced into a permissive cell line using any techniques well known in the art including DEAE-dextran mediated transfection, calcium phosphate-DNA co-precipitation, electroporation, lipofection, liposome fusion, protoplast fusion, microinjection, etc. Following transfer of the DNA (as linear or circular DNA), the transiently transfected cells are used to create the mixed cell cultures of the invention (described below) and these cultures are then inoculated with a specimen suspected of containing a virus capable of infecting the mixed cell culture following the introduction of the DNA.

When stably transformed cell lines are employed as the genetically engineered cell lines of the present invention, DNA comprising the chimeric viral promoter/reporter gene sequences are introduced into the recipient cell line (which is permissive for infection by the virus of interest) using any suitable technique (as described above). The chimeric gene sequence may contain a selectable marker within the same vector which contains the reporter gene or alternatively a second vector encoding a selectable marker may be co-transfected into the recipient cell line. following the introduction of the DNA sequences, the cells are subjected to grow in medium which requires the recipient cells to express the selectable marker. Example 1 herein provides an example of the generation of a stably transfected cell line containing a HSV gene promoter operably linked to a reporter gene.

The reporter gene construct contained within the genetically engineered cell line comprises a transcriptional initiation region from a virus (i.e., a viral gene promoter) and a structural gene encoding an enzyme operably coupled thereto such that the transcriptional initiation region regulates the expression of the reporter gene. After inoculation with the virus from which the promoter sequence was derived, the infected cell expresses detectable levels of the reporter gene product.

The genetic elements of the chimeric gene operate as a functional genetic unit to express the reporter gene product, which is preferably an enzyme, under the control of the transcriptional initiation region, or promoter. The promoter used in the chimeric gene is one that is capable of causing the expression of the reporter gene only in the presence of an infectious virus which encodes a transactivator specific for the viral promoter contained within the reporter gene construct. Thus, the enzyme is expressed only if an infectious virus is present in the specimen being analyzed. In a preferred embodiment the virus to be detected in the methods of the present invention is an infectious herpesvirus. As used herein, the term "infectious herpesvirus" denotes herpesvirus virions that are capable of entering cells and initiating a virus replication cycle, whether or not this leads to new virus production.

The promoter is preferably an inducible or transactivatable promoter isolated from the herpesvirus genome. An inducible or transactivatable promoter as used herein is a transcriptional initiation region of DNA that initiates transcription of a DNA sequence operably coupled thereto in response to a transactivating substance produced by the virus. Any inducible or transactivatable promoter from a herpesvirus desired to be detected by the assay may be used in connection with the chimeric gene of this invention. In particular, β-promoters from herpesviruses (i.e., promoters which drive the expression of intermediate early genes in a herpesvirus) are preferred for use as the promoter in this invention because of their ability to be transactivated. Examples of such promoters from HSV include the promoters from the UL42, UL29 and UL39 genes.

A particularly useful β-promoter is that isolated from Herpes simplex virus (HSV) type 1 gene UL39, which codes for ICP6, (the promoter being hereinafter referred to as the ICP6 promoter or when used in the identification of vectors and transformed cells, ICP6). The ICP6 promoter is strongly transactivated by the HSV virion-associated transactivator protein VP16 and expression can typically be detected within 3–6 hours after infection by HSV. Moreover, the ICP6 promoter does not cause constitutive expression in uninfected cells, and only causes expression of a gene operably coupled thereto in response to infection by a herpesvirus (i.e., the ICP6 promoter is induced in the presence of viral proteins present in the infected cell). This feature of the ICP6 promoter is particularly useful as it provides the specificity required of a useful diagnostic assay. In general, promoters useful in this invention should not cause constitutive expression in cells that have not been infected by the particular herpesvirus from which the promoter was obtained.

One embodiment of the present invention utilizes a promoter sequence isolated from a gene containing a DNA sequence encoding a ribonucleotide reductase or subunit of a ribonucleotide reductase. In one preferred embodiment of the present invention, the promoter of a HSV-1 UL39 gene that encodes a ribonucleotide reductase large subunit (ICP6) is operably coupled to a reporter gene. In another preferred embodiment of the present invention, the promoter of a HSV-2 gene that encodes a ribonucleotide reductase large subunit (ICP10) is operably coupled to a reporter gene.

The present invention can also utilize a promoter of a gene that corresponds to a UL39 gene of a Herpes Simplex Virus Type 1. The herpesvirus from which the gene is obtained can be any member of the herpesvirus family, and particularly, HSV-1, HSV-2, HCMV, VZV, EBV, HHV6 or HHV7, HHV8. By a gene that corresponds to a UL39 gene of a HSV-1 it is meant that the gene encodes an amino acid sequence that is a ribonucleotide reductase or subunit of a ribonucleotide reductase and the amino acid sequence is optimally aligned to the amino acid sequence encoded by a UL39 gene (i.e., the two sequences being compared are aligned such that the maximum degree of identity is obtained). Sequences which share more than 30% identity and preferably more than 50% identity and most preferably greater than or equal to 70% identity with the HSV UL39 gene product (i.e., identity on the amino acid level) are considered to be homologous (i.e., analogous) to the HSV UL39 gene. The optimal aligning of amino acid sequences can be determined by standard computer analyses according to identity of amino acids in the sequences as well as physiochemical and biological similarities of nonidentical amino acids (Nikas et al., *INS: Structure, Function, and Genetics* 1:376 384, 1986). An example, of a herpesvirus gene which is analogous to the UL39 gene is the UL45 gene of HCMV.

The identification and preparation of DNA sequences containing other promoters or promoters corresponding to the ICP6 promoter in other herpesvirus family members can thus be accomplished by using methods that are routine in the art. As noted above, all of the other human herpesviruses contain a DNA sequence encoding a ribonucleotide reductase large subunit and upstream of these DNA sequences are the promoter regions that initiate transcription. Therefore, an approach such as reported by Nikas et al. can be used to identify the DNA sequence in a given herpesvirus family member corresponding to a UL39 gene. As discussed above, the UL45 gene of HCMV is analogous to the UL39 gene of HSV; therefore the promoter of the UL45 gene of HCMV can be linked to a reporter gene to provide for an assay according to the present invention capable of detecting the presence of infectious HCMV in a specimen.

Isolation of the promoter of a gene corresponding to a UL39 gene is exemplified in the isolation of the HSV-2 promoter for the DNA sequence encoding ICP10. The large subunit of ribonucleotide reductase designated as ICP10 in HSV-2 and ICP6 in HSV-1 is encoded within the $U_L$ region of the viral genome (map units 0.554 to 0.584) [Wymer et al., *J. Virol.* 63:2773–2784 (1989); Nikas et al., *PROTEINS: Structure, Function, and Genetics* 1:376–384 (1986)]. One method for isolating the promoter for the DNA sequence encoding ICP10 is by PCR amplification of an approximately 600 bp fragment extending from approximately –500 bp to approximately +100 bp relative to the start point of transcription. The template for isolating the ICP10 promoter is obtained from cells infected with HSV-2 and primers are synthesized according to the reported sequence for the ICP10 promoter (Wymer et al., supra, at 2779). An approach similar to that outlined above can be used in identifying and isolating the promoters for genes encoding ribonucleotide reductase in other herpesvirus family members utilizing the known DNA sequences of the herpesvirus family members.

In earlier work Wymer et al. (supra, 1989) characterized the ICP10 promoter by introducing a chimeric ICP10 promoter-chloramphenicol acetyltransferase (CAT) gene construct into Vero (African green monkey) cells as well as into rat astrocytes, a human adenovirus-transformed cell line and a human laryngeal carcinoma cell line. The cells were used in a transient expression assay system and were not stably transformed. This group reported that the ICP10 promoter behaves like an immediateearly gene promoter inasmuch as the ICP10 promoter was shown to be stimulated by cotransfection with DNA that encodes a virion protein previously shown to transactivate immediate-early genes. In contrast to the present invention, Wymer et al. did not describe the use of a chimeric ICP10 promoter-reporter gene construct in an assay which permits the detection and typing of HSV.

In the methods of the present invention, the chimeric gene employed also includes a structural gene which codes for an enzyme which serves as the reporter or marker gene for the visual detection of a herpesvirus in a specimen. The enzyme is preferably one that can easily be assayed for or detected in a cell. One enzyme that has proved to be particularly useful for this purpose is β-galactosidase. Preferably, a bacterial β-galactosidase is used, and most preferably the β-galactosidase from *E. coli* that is encoded by the lacZ gene. β-galactosidase is preferred because of its wellcharacterized nature and the existence of a variety of methods to detect its presence; these well known assays permit the detection of the bacterial rather than the endogenous or cellular β-galactosidases. Other enzymes which can be employed as the reporter gene in the chimeric gene of this invention generally include hydrolases or oxidoreductases and, in particular, such enzymes as β-glucosidase, β-glucuronidase, β-hexosaminidase, luciferase, phospholipase, phosphatase, etc. In addition, the firefly luciferase gene, the cat gene and the GUS gene may be employed as reporter genes; vectors containing these gene sequences are commercially available.

The chimeric gene also includes a polyadenylation (poly A) and termination signal which may be integral with and native to the structural gene (i.e., the endogenous polyadenylation/termination signal)or may be obtained from a heterologous source. Examples of commonly used heterologous polyadenylation/termination signals include the simian virus 40 (SV 40) poly A signal, the HSV thymidine kinase gene poly A signal and the bovine growth hormone gene poly A signal (all three of these signals are present on a variety of commercially available vectors).

Once the desired chimeric gene has been prepared, it is preferably inserted into a plasmid which is then transfected into the desired cell line by standard and routine methods known to those skilled in the art. Sambrook, et al., *Molecular Cloning: A Laboratory Manual*, 2nd ed., Cold Spring Harbor Laboratory Press, N.Y. Cold Spring Harbor Laboratory (1989).

III. Generation Of Mixed Cell Cultures

The methods of the present invention employ mixed cell cultures which contain a permissive cell line mixed with a genetically engineered cell line containing the viral promoter/reporter gene construct. As described in detail in Examples 17–23 herein, mixed cell cultures are created by plating the permissive cell line into a suitable tissue culture vessel such as the wells of a multiwell tissue culture plate, shell vials and tube cultures. The permissive cell line is permitted to grow until confluent and then the genetically engineered cell line is seeded onto the permissive cell monolayer. The genetically engineered cell comprises a minority of the cells present in the mixed cell culture. The genetically engineered cell line may comprise between 1% and 20%, more preferably between 5% to 15% and most preferably about 10%, of the total amount of cells present in the mixed cell culture. Following the addition or seeding of the genetically engineered cell line onto the permissive cell monolayer, the mixed monolayers are incubated for approximately 16 to 24 hours prior to inoculation of the mixed cell monolayers with specimens suspected of containing infectious virus.

IV. Infection Of Mixed Cell Cultures

Following the incubation of the mixed cell monolayers, the monolayers are exposed to specimens suspected of containing infectious virus or with a stock viral culture (i.e., a positive control). Negative or uninfected controls are also employed; these cultures receive culture medium lacking any infectious virus. To inoculate a culture, an aliquot of specimen to be tested is placed in a suitable standard culture medium in standard culture vessels. The specimen may be any material which can be placed into a fluid or fluid from a person, animal or the environment such as blood, semen, nasopharyngeal swabs, cerebrospinal fluids and the like.

Inoculation may be performed using any method suitable for the type of culture employed (i.e., plate, shell vial or tube culture). When plate cultures or shell vials are employed, solutions suspected of containing infectious virus (or known control solutions) are dispensed into the wells of the plates and the shell vials may be centrifuged for about 1 hour at 700 g at room temperature. When shell vial and tube cultures are employed this centrifugation step in not required. Following inoculation (i.e., exposure of the monolayer to a specimen containing or suspected of containing infectious virus), the mixed cell monolayers are incubated at 37° C. The cell line and the specimen are cultured for a sufficient period of time for the virus infectious cycle to proceed. When the virus to be detected is a herpes virus, this time period is typically, between three and twelve hours and usually between three and six hours. If an infectious herpesvirus is present in the specimen, it will produce the transactivator necessary to induce the promoter and cause the expression of the marker gene which can then be detected and quantified by assaying for the presence of the reporter gene product. This method enables one to determine whether a certain specimen contains an infectious herpesvirus. Examples 17–23 provide further details regarding the inoculation of mixed cell monolayers when the virus of interest is a HSV.

V. Detection Of Reporter Gene Products

Following inoculation of the mixed cell cultures and incubation for a period sufficient to permit proliferation of the virus, the cell cultures are analyzed for the expression of the reporter gene product. The reporter gene product is detected using an assay suitable for the gene product which is encoded by the reporter gene. The art is well aware of suitable assays for the products of the cat gene, the lacZ gene, the GUS gene and the luciferase gene as well as other commonly used reporter genes.

A gene encoding β-galactosidase is one preferred reporter gene for use in this invention because of the numerous methods known to detect its expression and the relative sensitivity of such methods. Among these methods include histochemical assays involving a chromogenic or flurorogenic substrate which permits detection of β-galactosidase activity by a change in the color of the cell. The change in color can be detected macroscopically or microscopically. For example, methods are known which use a chromogenic substrate such as 5-bromo-4-chloroindolyl-β-D-galactopyranoside, which turns the cells blue in the presence of β-galactosidase, or a fluorogenic substrate such as fluorescein de-β-D-galactopyranoside (FDG), 3-carboxyumbelliferyl-β-D-galactopyranoside or 5-dodecanoylaminofluorescein di-β-D-galactopyranoside ($C_{12}$ FDG) which stains the cells intensely green, to detect β-galactosidase activity. Automated colorimetric assays are also available for detection of β-galactosidase activity. One such assay uses ONPG as the substrate for β-galactosidase activity in a cell lysate and the enzyme activity is detected by spectrophotometry. An automated fluorescence assay is also known.

The detection of β-galactosidase by a fluorescence microscopy method, as further described in Example 9, in the assay of the present invention is advantageous for a variety of reasons. FDG is relatively impermeable to cells and previously described protocols for delivery of FDG into cells involve osmotic shock in addition to careful temperature regulation and the use of competitive and noncompetitive inhibitors of β-galactosidase. These and other complications are necessary for quantitative enzymatic measurements. To detect HSV-infected cells by the method of this invention, however, all that is required is that sufficient FDG enter the cells for the virus-induced β-galactosidase to cleave sufficient FDG to release sufficient fluorescein to allow the cells to be brightly fluorescent. It may be that HSV-infected cells are more permeable to FDG than uninfected cells. In addition, the fact that BHK cells have little in the way of endogenous β-galactosidase activity or autofluorescence, and the fact that no constitutive β-galactosidase activity has been observed in cells of the present invention results in virtually no background fluorescence in uninfected cells. The combination of all these factors contribute to the high signal to noise ratio (i.e., easy visual discrimination between infected and uninfected cells) despite a simple method to deliver the FDG to the cells.

Previously described procedures to detect β-galactosidase positive cells using fluorogenic substrates involved cooling the cells below the membrane freezing point after exposure to the fluorogenic substrate to prevent fluorescein from diffusing out of the cells. This adds a complication to the fluorescence microscopy (i.e., it would require a cooling chamber on the microscope) which was found not to be necessary when this means for detection was used with the method of this invention. The cells can be held at ambient temperatures so long as the cells are observed within 15 minutes from the time of exposure to the FDG without loss of sensitivity.

Another particularly useful reporter gene for use in the method and cell line of this invention is the gene encoding firefly luciferase. The expression of luciferase may be detected by known luminometric methods using luciferin as the enzyme substrate. The use of luciferase as the reporter gene provides an enzymatic assay that is more sensitive than the calorimetric or fluorometric β-galactosidase assay and is also more amenable to the development of an automated assay which can detect a single infectious virus.

VI. Detection Of Infectious Virus And Typing Of Infectious Virus In Specimens

Importantly the methods of the present invention which employ mixed cell cultures permit both the detection and the typing of infectious virus present in a specimen. This ability to type or distinguish between two closely related viruses, such as HSV-1 and HSV-2 present in a sample using a single mixed cell culture is a significant improvement over methods currently available for the detection and typing of viruses. This is a tremendous advantage in terms of diagnostic ease and efficiency.

Early in the development of an HSV diagnostic test [ELVIS™ HSV; Diagnostic Hybrids; this assay employs the ELVIS™ HSV cell line, a transgenic (i.e., a genetically engineered) BHK21 line with a β-galctosidase reporter gene activated by HSV 1 or 2 infection of the cell] which uses the stable cell line BHKICP6LacZ to detect HSV-1 and 2 after a 16–24 hour culture amplification period, studies were initiated to use this cell line in an antiviral susceptibility test. The planned approach was to absorb 100–200 plaque forming units (pfu) onto the BHKICP6LacZ cell monolayer in a multiwell plate, add maintenance medium (no drug) and maintenance medium with various concentrations of antiviral agent to the appropriate wells, allow the virus time to go through repeated cycles of genomic replication virus packaging, release of new infectious virus and re-infection of uninfected cells, whereby the viral infection cycle would commence again with subsequent release of more virus. In this model the no wells represent a situation where viral proliferation to cells beyond the primary infected cell can take place in an uninhibited manner. As virus spreads on the monolayer from cell to cell, the tissue culture becomes toxified by the viral replication process and undergoes morphologic changes, oftentimes characterized by the term cytopathic effect (CPE) because of the physical perturbation and destruction whiich occurs to the uniformity of the healthy cell monolayer. These changes can be observed by microscopy and range from rounding of cells and detachment from their primary anchorage site, to the formation of giant, multi-nucleated cells formed through syncytia. These changes can usually be differentiated from the uninfected, healthy tissue culture cells. Conversely, the spread of virus throughout a monolayer can be inhibited by the addition of increasing doses, of an anitviral chemotherapeutic agent to the culture medium for the incubation period, usually 48–96 hours, to the extent that the drug is sub-toxic to the cell-monolayer. The ultimate goal was to use the BHKICP6LacZ cells as a homogeneous monolayer for assessing the degree of inhibition of viral spread, or viral proliferation, in the presence of known or potential, inhibitory agents by measuring the expression of a reporter gene which was inducible by HSV infection. A useful antiviral for inhibiting the proliferation of HSV-1 and 2 in vivo and in vitro without major toxicity problems is acyclovir (ACV) (Bean, B. 1992. *Clin. Microbiol. Rev.* 5:146–182). Unfortunately, each primary infected cell or "start" of the infectious process, induced expression of high levels of reporter gene even though the viral spread did not take place when ACV was added. Color is generated from primary infected cell "starts" because ICP6 transactivators do not require viral replication in order to activate the inducible expression of the ICP6 promoter. Thus, although conditions appropriate for inhibiting the spread of the virus were established, and thus, viral CPE was not observed indicating that viral proliferation was inhibited, report gene product (β-galactosidase) was produced. The amount of color depended upon the titer of the original viral inoculas. "Starts" represented a background signal to the assay and this phenomena appeared to eliminate the use of BHKICP6LacZ cells in antiviral drug susceptibility testing.

It was surprisingly found that the use of engineered cells in low numbers as indicator cells in a monolayer of predominately (a majority), non-reporter, traditional cells permissive for the virus of interest eliminated the background problem to the extent that it permitted the use of engineered cells in antiviral drug susceptibility. It was generally found that background staining due to "starts" was reduced 100-fold through the use of mixed cell monolayers comprised of a ratio of 1:100 (engineered to non-engineered permissive cell lines). Specifically, by mixing a ratio of 100 MRC-5 cell per BHKICP6LacZ cells and allowing a monolayer to form, infections could be set at 200 pfu viral input and only produce 2 "starts." While it is not intended to limit the scope of the invention, it is believed that in a monolayer comprised of a significant majority of permissive traditional cells for the virus of interest along with an engineered cell line containing a reporter for the virus of interest, the virus of interest must replicate and be passed to a reporter cell before the specific enzyme produced by the specifically engineered cells for the virus of interest would be induced. Thus, the signal generated is a quantitative evaluation of the degree of inhibition of a virus by an antiproliferative agent, such as ACV.

Mixed cell monolayers in addition to effectively reduced background signal caused by "starts" produced other unexpected results as well. The amount of color generated in the mixed cell monolayers was in excess of what one would expect based on the number of reporter/indicator cells in the mix. While it is not intended to limit the scope of the invention it is believed that mixed cell monolayers enhance a subtle diagnostic difference first observed with the histochemical detection of viral induced HSV-1 and 2 on 100% BHKICP6LacZ, i.e, HSV-1 induced cells produced a more intense histochemical staining than HSV-2.

The possibility that the functional homology of the HSV-1 transactivator mechanism for the HSV-1 promoter ICP6 was greater than the induction of the HSV-I was investigated. ICP10, the HSV-2 promoter homologue of the HSV-1 ICP6 promoter, was cloned by PCR, transfected into a BHK cell line, and isolated by antibiotic selection using gentamicin to see if the staining of HSV-2 infected BHKICP10LacZ cells would be significantly stronger than the signal induced by HSV-1 on the ICP10 containing cells. Surprisingly, the cell line with the HSV-2 promoter behaved similarly to the HSV-1 promoter cell line. While it is not intended to limit the scope of the invention it is believed that the BHKICP6LacZ cell line is a dominant transactivator and that induction of HSV-1 on either type promoter sequence was approximately 10-fold greater than the HSV-2 inducibility regardless of the promoter clone used.

When the BHKICP6LacZ cell line was tested in the ELVIS HSV diagnostic kit format, it was observed that the homogenous cells did not do well when cultured for any period beyond 36–48 hours. The BHKICP6LacZ cells appeared highly aged and deteriorated with a concomitant reduction in analytical sensitivity. This lack of stability beyond a 48 hour time framne precludes the use of the 100% cell line in a tube culture format which requires 7 days of incubation.

It was surprisingly found that the use of mixed cell lines comprised of a majority of a non-engineered cell line permnissive for the virus of interest in combination with an engineered cell line which is capable of reporting the presence of the virus of interest permits a seven day tube culture assay. A non-engineered cell line permissive for the virus of interest allows the proliferation and identification of CPE while the virus specific engineered line in the cell bed confirms that the effects are indeed due to the virus of interest.

In a preferred embodiment MRC-5 cells are employed as the permissive cell line present in a majority with BHKICP6LacZ cells, a genetically engineered cell line in a mixed cell culture.

The genetically engineered cells are specific for HSV infection, since β-galactosidase induction occurs only with HSV infection. This system eliminates the scraping of infectious material from the tube and processing on a slide as is done for fluorescent antibody confirmation. The safety, speed and simplicity of this mixture design provides a significant improvement over current confirmation protocols. In a particularly preferred embodiment the non engineered MRC-5 cells are mixed in a ratio of 90:10 with the genetically engineered cells.

In one embodiment the cells are planted simultaneously, in various ratios of the two cell types as determined by optical density. In a preferred embodiment the permissive cells are planted, and the monolayer is allowed to come to approximately 95% confluence and then planting or "seeding on" the specific engineered cells for the virus of interest at a predetermined concentration. The seeded ELIVIS™ HSV cells insinuated into the preformed MRC-5 monolayer and allowed easy identification of HSV CPE. The ratio of MRC-5 to Elvis HSV cells of 90:10 was selected on the basis of experimentation with a range of ratios from 1% to 20%. The requirement of primary importance was that when CPE due to HSV was observed, ELIVIS™ HSV blue stained cells would always be detected to confirm that HSV was present. The 10% mixture provided numerous blue stained cells in cases of minimal or early CPE, yet retained the monolayer appearance more typical of MRC-5. Higher ratios of Elvis HSV cells in the mixture show more blue cells, but compromise the MRC-5 appearance of the monolayer (as described in further detail in the examples below).

EXPERIMENTAL

The following examples serve to illustrate certain preferred embodiments and aspects of the present invention and are not to be construed as limiting the scope thereof.

In the experimental disclosure which follows, the following abbreviations apply: M (molar); mM (millimolar); $\mu$M (micromolar); mol (moles); mmol (millimoles); $\mu$mol (micromoles); nmol (nanomoles); gm (grams); mg (milligrams); $\mu$g (micrograms); pg (picograms); L (liters); ml (milliliters); $\mu$l (microliters); cm (centimeters); mm (millimeters); $\mu$m (micrometers); nm (nanometers); °C. (degrees Centigrade); AMP (adenosine 5'-monophosphate); cDNA (copy or complimentary DNA); DNA (deoxyribonucliec acid); ssDNA (single stranded DNA); dsDNA (double stranded DNA); DNTP (deoxyribonucleotide triphosphate); RNA (ribonucleic acid); PBS (phosphate buffered saline); g (gravity); OD (optical density); HEPES (N-[2-Hydroxyethyl]piperazine-N-[2-ethanesulfonic acid]); HBS (HEPES buffered saline); SDS (sodium dodecylsulfate); Tris-HCl (tris[Hydroxymethyl]aminomethane-hydrochloride); Klenow (DNA polymerase I large (Klenow) fragment); rpm (revolutions per minute); EGTA (ethylene glycol-bis($\beta$-aminoethyl ether) N, N, N', N'-tetraacetic acid); EDTA (ethylenediaminetetracetic acid); bla ($\beta$-lactamase or ampicillin-resistance gene); ORI (plasmid origin of replication); ATCC (American Type Culture Collection, Rockville, Md.); Becton Dickinson (Becton Dickinson, Bridgewater, N.J.); Costar (Corning Costar, Cambridge, Mass.); Diagnostic Hybrid (Diagnostic Hybrids, Inc., Athens, Ohio); Falcon (division of Becton Dickinson Labware, Lincoln Park, N.J.); FMC (FMC Bioproducts, Rockland, Me.); Gibco/BRL (Gibco/BRL, Grand Island, N.Y.); HyClone (HyClone, Logan, Utah); NEB (New England Biolabs, Inc., Beverly, Mass.); Perkin-Elmer (Perkin-Elmer, Norwalk, Conn.); Pharmacia (Pharmacia Biotech, Pisacataway, N.J.); Promega (Promega Corp., Madison, Wis.); and Sigma (Sigma Chemical Co., St. Louis, Mo.).

EXAMPLE 1

This example illustrates the preparation of a susceptible cell line genetically engineered to enable it to detect infectious herpes simplex virus.

Baby hamster kidney (BHK-21) cells were obtained from C. Hahn and C. Rice (Washington University, St. Louis, Mo.). The cells were propagated in MEM medium (Gibco-BRL, Gaithesburg, Md.) supplemented with 7% fetal calf serum (Gibco). These cells were co-transfected with pYBICP6LacZ and pMAMneo by the liposomal transfection protocol [e.g., Ausubel et al., Current Protocols in Molecular Biology (1987) John Wiley & Sons, Inc., Unit 9.4] using reagents obtained from Gibco-BRL. The essential features of plasmid pYBICP6LacZ are shown in FIG. 1. This plasmid was prepared by isolating a BamHI fragment from pD6p, obtained from Dr. Sandra Weller (Univ. of Conn.), which contains the ICP6-LacZ fusion cassette as described in Goldstein and Weller, J. Virol. 62:196–205 (1988), and subcloning this fragment into the BamHI site of the vector pUC8. Plasmid pMAMneo contains the SV40 early promoter-neomycin resistance gene cassette and was purchased commercially from Clontec, Palo Alto, Calif.

The transfected cells were placed in a culture medium containing G418 (Geneticin, Sigma, St. Louis, Mo.) and G418 resistant colonies were selected. Several cell lines were identified as being resistant to G418 and were tested for $\beta$-galactosidase activity. One such cell line, BHKICP6LacZ-5, displayed no detectable $\beta$-galactosidase activity after mock infection and pronounced activity following infection with HSV. This cell line was selected for further studies.

EXAMPLE 2

This example illustrates the ability of the cell line of this invention to detect infectious herpes simplex virus in a specimen.

Cells from cell line BHKICP6LacZ as described in Example 1 were obtained and infected with HSV-1 at various multiplicities of infection (M.O.I.) in standard tissue culture medium. The cells and the virus were allowed to remain in culture for 12 hours after which the cells were assayed for $\beta$-galactosidase activity by the histochemical staining method. The cells were washed three times in phosphate buffered saline (PBS) pH 7.2 and fixed in a solution of 2% formaldehyde and 0.4% glutaraldehyde in PBS for 5 minutes at 4° C. The cells were then washed twice in PBS and incubated for 2 hours at room temperature in the histochemical staining solution. The solution comprises 1 mg/ml X-GAL (5-bromo-4-chloro-3 indolyl-$\beta$-D-galactopyranoside), 4 mM potassium ferrocyanide, 4 mM potassium ferrocyanide, 2 mM MgCL$_2$ in PBS. The staining solution was made up fresh before use with concentrated stock solutions of each reagent. The X-GAL stock solution was 40 mg/ml in N, N-dimethylformamide. The reaction was stopped by washing the cells with PBS. The cells were analyzed directly and by light microscopy and stored in PBS at room temperature.

At the higher m.o.i., the blue stain was evident macroscopically and as the m.o.i. decreased, microscopic examination of the cells which did not appear to stain blue by direct inspection revealed individual blue cells among a predominance of unstained cells. Microscopic analysis of the infected cells revealed blue stained cells. Control cells subject to no infection and mock infection exhibited no blue staining of the cells.

EXAMPLE 3

This example illustrates the ability of the cell line and assay of this invention to quantitate the number of infectious herpes simplex virus in a specimen.

Herpes simplex virus is routinely quantified by determining the titre of infectious virions as plaque forming units (pfu) per milliliter (ml). A solution known to contain herpes simplex virus, but of unknown amount, was submitted to a standard quantitative plaque assay. An aliquot (0.5 ml) of the solution was placed into a tube with 4.5 ml of culture medium constituting a 10-fold dilution. This diluted sample was then diluted 10-fold in like manner serially until a 10,000,000 dilution was achieved in the final tube. We now had tubes with $10^{-1}$ through $10^{-7}$ the concentration of virus of the original solution. An aliquot (0.5 ml) of the highest three dilutions ($10^{-5}$, $10^{-6}$, $10^{-7}$) was added to a monolayer of BHK cells in 10 cm² wells. This was done in duplicate. After allowing the virus to absorb to the cells for one hour, the media was aspirated from the well and replaced with media containing neutralizing antibody to herpes simples virus (to restrict spread of the virus to a focal area of the monolayer). After 48–72 hours circular area of dead cells (plaques) appeared in the monolayer. The number of plaques in each well was counted. Wells with too many plaques (>100) or too few plaques (<10) were not counted. In one assay, 21 plaques were seen on one of the duplicate wells using the $10^{-7}$ dilution and 17 plaques on the other duplicate. The titre of the starting solution was then calculated using the following formula:

$$\frac{\text{average \# plaques/well}}{\text{dilution}} \times \frac{1}{\text{volume added to the cells}} = \text{pfu/ml}$$

Therefore in the above case the average # of plaques= 17+21/2=19. The dilution was $10^{-7}$. The volume added was 0.5 ml.

The titre was therefore:

$$\frac{19}{10^{-7}} \times \frac{1}{0.5} = 38 \times 10^7 \text{ or } 3.8 \times 10^8$$

The same exact dilutions were also inoculated onto BKHICP6LacZ-5 cells in exactly the same manner except that after 16 hours the cells were fixed and histochemically stained for β-galactosidase activity (16 hours is less than growth cycle of herpes simplex virus and thus too short a time period for a plaque to form). Blue cells were then counted in each well with an inverted light microscope. In duplicate wells derived from the $10^{-7}$ dilution, 20 and 23 blue cells were seen. A blue cell is referred to as a blue forming unit (bfu) and the number of bfu per ml was calculated using the same formula as above:

$$\text{average \# blue cells} = \frac{20+23}{2} = 21.5$$

$$\frac{\text{bfu}}{\text{ml}} = \frac{21.5}{10^{-7}} \times \frac{1}{0.5} = 43 \times 10^7 \text{ or } 4.3 \times 10^8$$

In summary, a virus containing solution was diluted and the identical dilutions were submitted to the standard assay to quantitate infectious herpes simplex virus and to the histochemical assay using BHKICP6LacZ cells and the calculated number of plaque forming units per ml closely approximated the number of bfu per ml. The titers ($3.8 \times 10^8$ pfu/ml and $4.3 \times 10^8$ bfu/ml) are essentially equivalent from a virologic point of view given the intrinsic variability of a quantitative plaque assay. Therefore as a pfu is used as an indicator of a single infectious virus, a bfu also can also be used as an indicator of a single infectious virus.

EXAMPLE 4

This example illustrates the ability of the assay of this invention to rapidly detect HSV-1 in a specimen.

Figure 2:
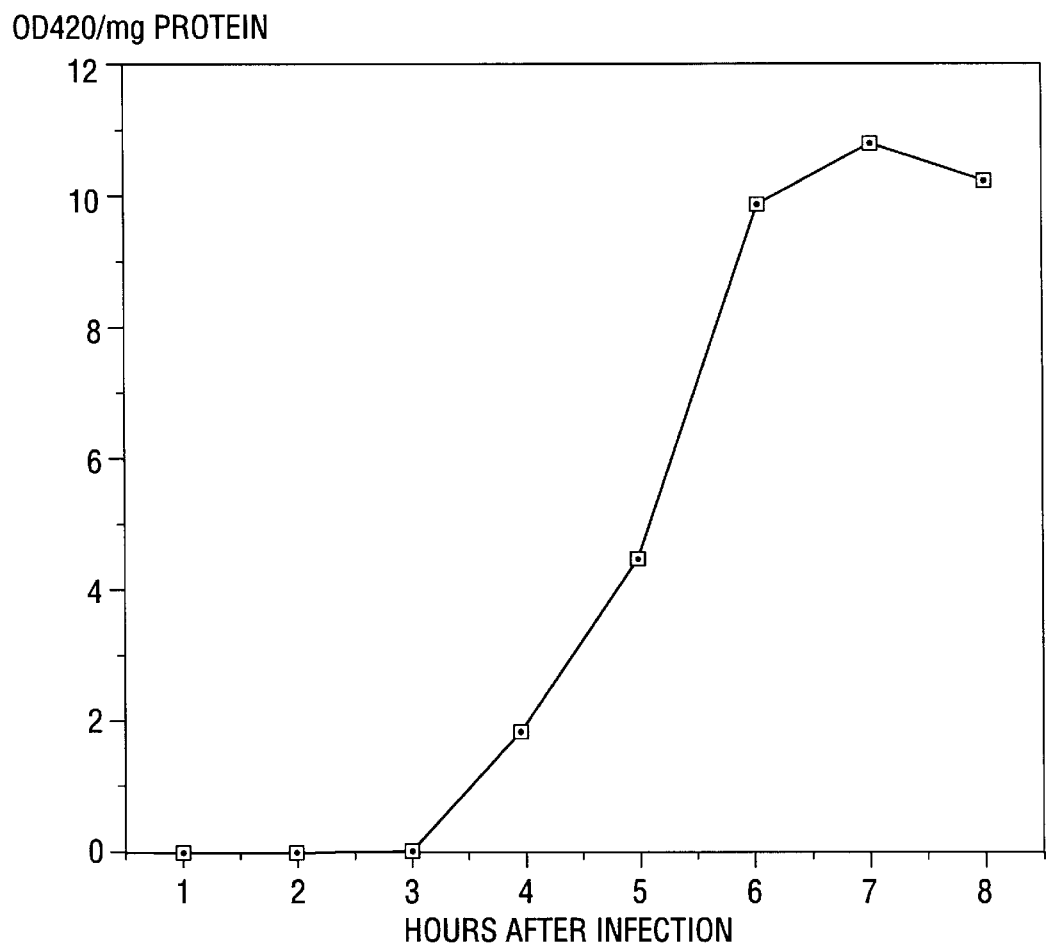
FIG. 2 is a graphical representation of β-galactosidase activity in Herpes Simplex Virus-infected BHKICP6LacZ cells at various timepoints after infection as measured by a colorimetric assay on cell lysates.

BHKICP6LacZ cells as described in Example 1 were infected with HSV-1 at a m.o.i. of 10 and 0.1 as previously described in Example 2. At various times after the cells were infected, cells were removed, lysed and assayed for β-galactosidase activity by a colorimetric assay. The colorimetric assay was performed on whole cell lysates using O-nitrophenyl-β-D-galactopyranoside (ONPG, Sigma, St. Louis, Mo.) as the substrate in a standard calorimetric β-galactosidase assay as described in Maniatis, et al., Cold Spring Harbor, N.Y., Cold Spring Harbor Laboratory (1990). Protein determinations of the lysates were performed using a commercially available kit based on the Bradford method (Bio-Rad, Richmond, Calif.). Enzyme activity was detected approximately four hours after infection and peaked at six hours after infection for the cells infected at a high m.o.i. FIG. 2 presents a graphical representation of the detection of β-galactosidase activity v. time by this assay.

As a comparison, cells subject to the same method of infection were assayed by the histochemical staining method as described in Example 2. A few blue staining cells could be seen approximately three hours after infection and greater than and 90% of the cells stained blue after six hours for the cells infected with a high m.o.i. The cells infected with a low m.o.i. did not develop blue staining cells until approximately six hours after infection.

EXAMPLE 5

This example illustrates the specificity of the cell line and method of this invention to detect only the presence of HSV in a specimen.

Monolayers of BHKICP6LacZ-5 cells were inoculated, separately, with specimens known to contain other viruses and assayed histochemically for β-galactosidase activity. Infection of BHKICP6LacZ cells with four different viruses resulted in no β-galactosidase expressing cells.

Three virus specimens were obtained from the Diagnostic Virology Laboratory at St. Louis Children's Hospital. Separate specimens were obtained which contained human cytomegalovirus (HCMV), varicella zoster virus (VZV), and adenovirus type 5. Each of the specimens contained an amount of virus derived from a 4+ cytopathic effect (a semiquantitative measure of the amount of virus in a sample whereby 1+ equals the least amount and 4+ the highest amount). In addition, a laboratory strain of Sindbis virus (a Togavirus) with a titre of $10^7$ pfu/ml was grown in the laboratory. A 0.15 ml aliquot of each of these viruses was separately inoculated onto monolayers of $2.0 \times 10^6$ BHKICP6LacZ-5 cells. (This amount of each virus when inoculated onto the cell line normally used to grow these viruses resulted in a 4+ cytopathic effect characteristic of each virus). At 24 hours after infection with each of these viruses the BHKICP6LacZ cells were fixed and histochemically stained for β-galactosidase activity. BHKICP6LacZ-5 cells infected with none of the four viruses exhibited any histochemical evidence for β-galactosidase activity i.e., no blue cells were seen microscopically. HSV type 2 infection of BHKICP6LacZ cells resulted in β-galactosidase activity in a manner indistinguishable from HSV type 1. Thus this method is specific for HSV-1 and HSV-2 (collectively HSV).

EXAMPLE 6

This example illustrates the use of the cell line and assay of this invention for analyzing clinical specimens for the presence of HSV.

A prospective study was done in a diagnostic virology laboratory. During the period between Sep. 9, 1991 and Nov. 28, 1991 all specimens the laboratory received for the purpose of detecting HSV were submitted to both the standard cytopathic effect (CPE) assay and the method of this invention. A total of 96 specimens were processed from 94 patients. Specimens were derived from multiple body sites (swabs of cervical, skin, mouth lesions, bronchoalveolar lavage specimens, etc.). All specimens were received in a standard physiologic transport medium.

For the standard CPE assay, a 0.2 ml aliquot of each specimen was inoculated into a roller tube containing a monolayer of a tissue culture cell line (rabbit skin fibroblasts) obtained commercially and commonly used to grow HSV. After one hour on a roller apparatus at 37° C., fresh tissue culture medium (minimal essential medium +5% calf serum) was added and the cells were returned to the roller apparatus and the 37° C. incubator. The following day, and at 12 hour intervals for up to 7 days, the cells were examined microscopically, by a trained diagnostic virology technician using an inverted light microscope, for evidence of CPE characteristic of HSV. The results of this analysis were part of the laboratory's normal diagnostic function and were reported to the physician who ordered the test.

At the same time that the CPE assay was set up another assay using the method of this invention was set up in parallel. A 0.2 ml aliquot of each specimen was also inoculated onto BHKICP6LacZ-5 cells which were being cultured on the exact same type of roller tube used for the commercially purchased cells mentioned above. The cells were processed in the same manner except that on the day after inoculation (16–24 hours depending on when the time of day the specimen was received by the laboratory and done at the convenience of the technician) the cells were fixed and histochemically stained for β-galactosidase activity. The cells were then examined under a light microscope and scored for the presence of blue cells. The results are shown in Table I below.

TABLE I

| # Specimens | CPE | β-gal. Stain |
|---|---|---|
| 31 | + | + |
| 62 | − | − |
| 0 | + | − |
| 3 | − | + |

As shown by the data in Table I, all 31 specimens that contained HSV as evidenced by the positive CPE assay were positive in the β-galactosidase staining assay i.e., there were no false negatives. It should be noted that the β-galactosidase staining was done "blindly" i.e., without knowledge of the CPE results. In fact, 15 of the 31 CPE positive specimens did not become positive until day 2 or more. Therefore at the time of the histochemical staining these 15 CPE positives were still read as negative. As can be seen in Table I, 3 specimens that were read as positive by the technician for β-galactosidase staining were negative by CPE. Two of these were from the same patient and were from an oral source. Examination of the histochemically stained cells revealed that the blue cells were not, in fact, fibroblasts (as are BHKICP6LacZ-5 cells) but obviously epithelial cells. These cells likely came from the patient's mouth and the cells likely were colonized with a bacteria expressing β-galactosidase. Consistent with this notion, we repeated the assay on these specimens and noted that these cells stained blue at time zero before HSV would have time to induce β-galactosidase activity. The third specimen than was CPE-negative, β-galactosidase positive displayed a single blue cell whereas all the other 31 positives had many blue cells. This false negative result remains unexplained. No virus (HSV or otherwise) was cultured from this specimen. Finally two of the CPE-negative β-galactosidase negative specimens grew varicella zoster virus (VSV), confirming our laboratory observation of the specificity of the method of this invention for HSV.

In summary, the method of this invention, when compared to the standard laboratory method to detect HSV on clinical specimens, showed excellent (100%) sensitivity (31/31). It was also more rapid than the standard method in that all 31 positives were detected at 24 hours or less compared to 16 of 31 CPE positives at 24 hours and the remaining 15 not being noted to be positive until 48 or 72 hours.

EXAMPLE 7

This example demonstrates the ability of the firefly luciferase gene to be used as a reporter gene to detect HSV. The rationale for using luciferase is that the enzymatic measurement of luciferase on cell lysates is far more sensitive than β-galactosidase.

Figure 3:
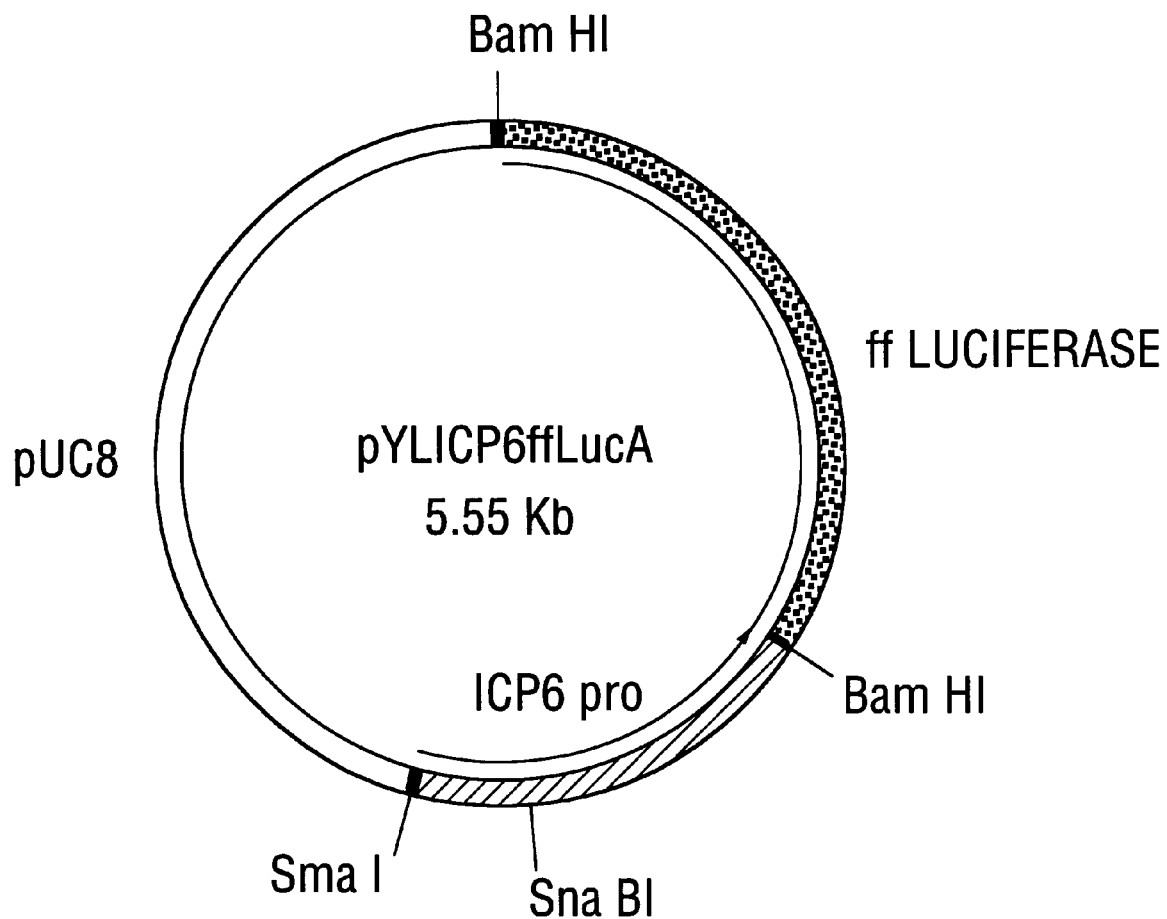
FIG. 3 is a schematic representation of pYLICP6ffLucA.

A cell line was derived from BHK cells using the method described in Example 1. BHK cells were stably transformed with pMAMneo and pYLICP6ffLucA (which contains a ICP6-firefly luciferase chimeric gene), a map of which is shown in FIG. 3, using G418 selection. pYLICP6ffLucA was prepared by inserting a 1.9 kb fragment from pTS/T7Luc (Clontec, Palo Alto, Calif.) which contains the luciferase gene into the BamHI site of pDCICP6-1B which has a BamHI site at the 3' end of the ICP6 promoter. The ICP6:luciferase chimeric gene is not expressed as a fusion protein. One such stably transformed cell line was named BHKICP6LucA6.

Figure 4:
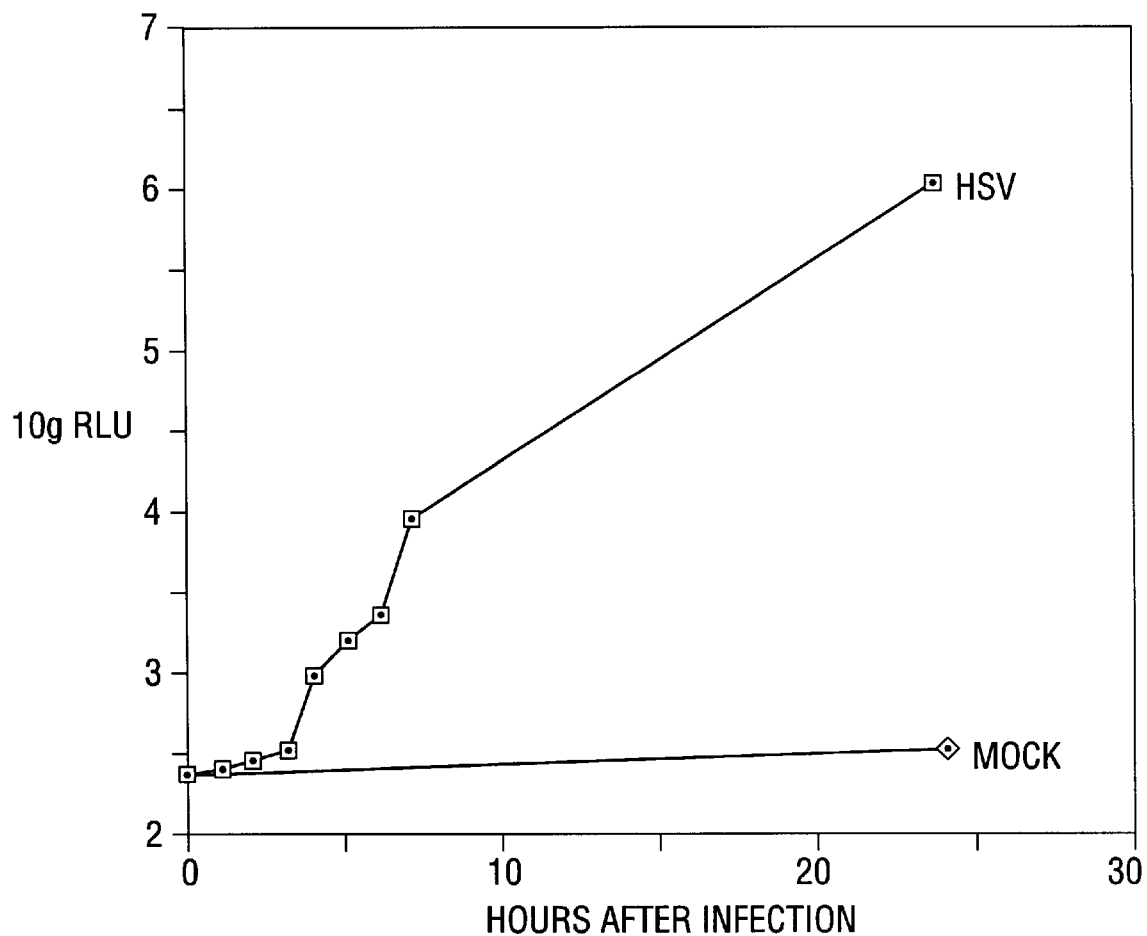
FIG. 4 is a graphical representation of luciferase activity in Herpes Simplex Virus-infected BHKICP6LucA6 cells at various timepoints after infection as measured by luminometry on cell lysates.

BHKICP6LucA6 cells were grown as monolayers on 24 well tissue dishes ($2.5-5.0 \times 10^5$ cells per well). The cells were then infected with $10^3$ pfu of HSV per well. At various times after infection the cells were lysed and assayed for luciferase activity. The procedure was as follows. The media (MEM+10% fetal calf serum) was aspirated, the cells were washed 2× with 1 ml of phosphate buffered saline, pH 7.4, and then 0.1 ml of lysis buffer (50 mM Tris-MES pH 7.8, 1 mM DTT, 1% Triton X-100) was added. The dish was placed on a rotating shaker for 10 minutes at ambient temperature. 0.05 ml of each cell lysate was then assayed for luciferase activity in the following protocol. 0.150 ml of luciferase reaction buffer (final reaction concentrations: 50 mM Tris-MES, pH 7.8, 10 mM magnesium acetate, 2 mM ATP) as added to a 12×75 mm disposable glass tube. 0.05 ml of the cell lysate was added and mixed gently. The tube was placed in a luminometer which automatically injects 0.1 ml of 1 mM luciferin and then measures the release of photons over a 10 second period of time. A number is recorded as relative light units (RLU) as a measure of the amount of luciferase activity. Typically 0.05 ml of buffer lacking luciferase, or 0.05 ml of a BHK cell-lysate, gives a value of 150 to 200 RLU in this assay. Uninfected BHKICP6LucA6 cell lysates give $4-8 \times 10^4$ RLU per cell or 300–400 RLU for a 0.05 ml lysate of $2.5 \times 10^5$ cells. FIG. 4 shows a time course of luciferase activity after infection of BHKICP6LucA6 cells infected as described above. As can be seen, luciferase activity increases well above uninfected cell background by 4 hours after infection and by 24 hours the luciferase activity is 5000-fold above the uninfected cell background. The data illustrated in FIG. 4 represents $10^3$ infected cells and $2.5 \times 10^5$ total cells in the assay; the calculated RLU/infected cell to RLU/uninfected cell ratio is at least 500,000.

EXAMPLE 8

This example illustrates the ability of the BHKICP6LucA6 cell line and the method of Example 7 to detect a single infectious HSV in an enzymatic luciferase assay on cell lysates.

BHKICP6LucA6 cells were cultured in 24 well dishes. The cells were inoculated with a solution of diluted HSV. Four dilutions were made with concentrations of virus (based on a predetermined titre done as described in Example 3) of 5 pfu/ml; 2.5 pfu/ml; 0.5 pfu/ml; and 0.025 pfu/ml. 0.2 ml of each of these diluted HSV solutions were then inoculated into 9 separate wells and 6 wells were uninfected (i.e., 42 well total). Therefore 6 wells got no virus. 9 wells 1 pfu, 9 wells 0.5 pfu, 9 wells 0.1 pfu, and 9 wells 0.05 pfu. Since an HSV pfu is a discrete entity, these numbers actually represent a certain probability of each well getting infected or not and that probability can be calculated using a standard Poisson equation. The cells were then harvested for luciferase activity as described in Example 7. In parallel these same exact dilutions were inoculated onto BHK cells and microscopically observed daily for CPE for 7 days.

Figure 5:
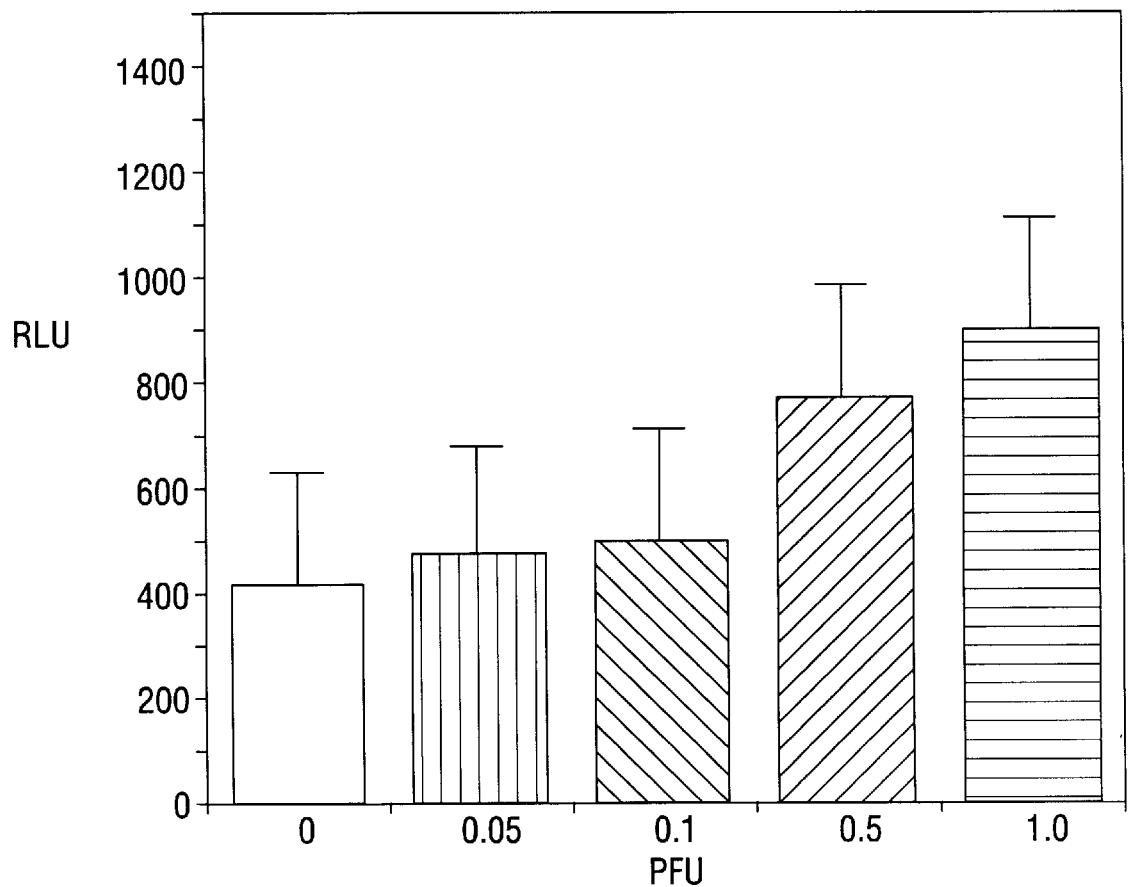
FIG. 5 illustrates the average luciferase activity as a measure of the amount of virus added to an assay.
Figure 6:
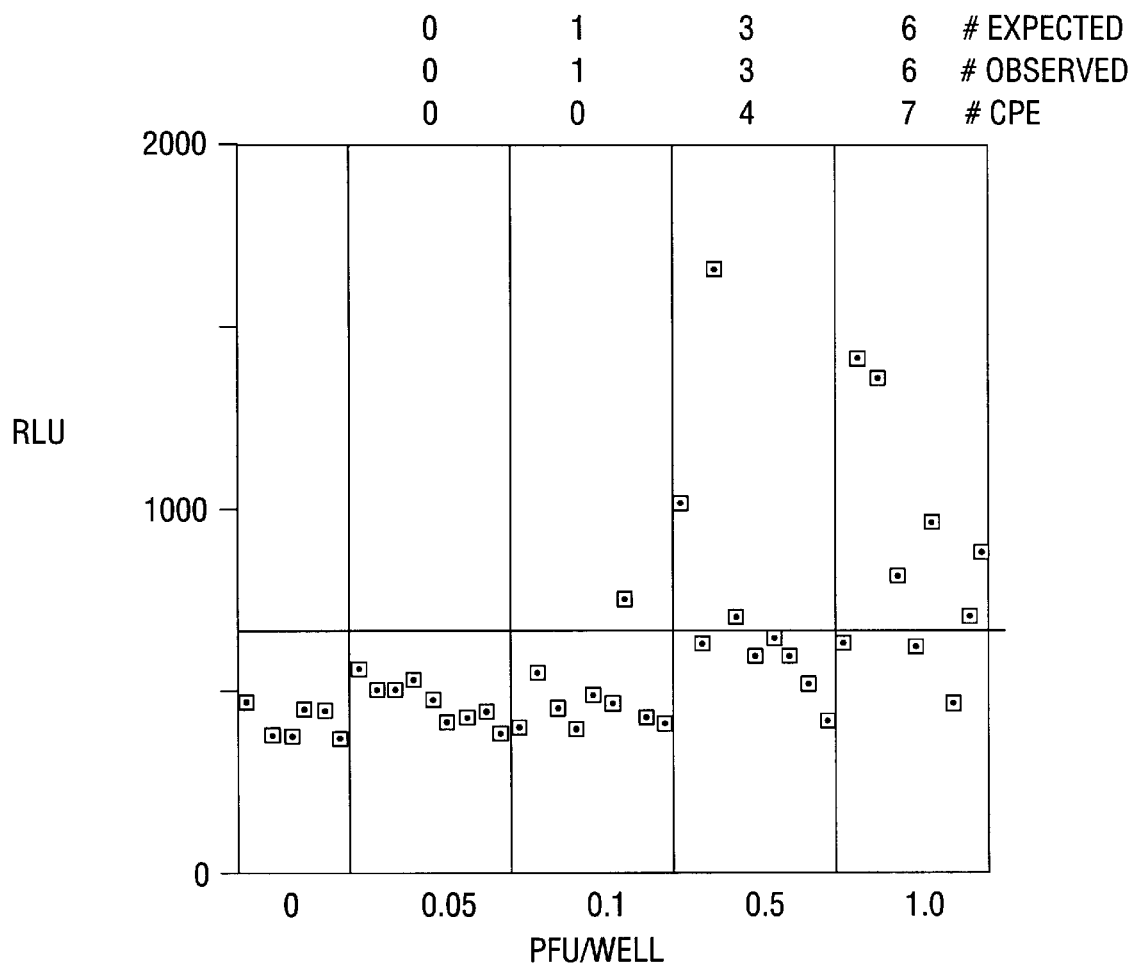
FIG. 6 illustrates the individual data points of luciferase activity used to obtain the average luciferase activity values in FIG. 5.

FIG. 5 shows the average luciferase activity as a measure of the amount of virus added. Although there is a trend toward increased activity with more virus it is not statistically significant. When the individual data points are analyzed (FIG. 6), however, it is clear than an individual pfu can be detected. The # expected equals the number of wells that should receive a PFU based on Poisson probability. The # CPE equals the number of wells in which CPE was seen on the BHK cells. The # Observed equals the number of wells in which the measured luciferase activity was above uninfected cells by an amount predicted to be present in a single infected cell. (This was determined by infecting 3 wells with 100 pfu and the RLU measured from those cells was averaged and divided by 100). There is clearly a good correlation between the Poisson predicted # of infected wells and the # CPE positive wells which shows that our virus titre is accurate. The good correlation between these numbers and the number of wells with higher luciferase activity than the uninfected cell background indicates that this method can detect a single infected cell and thus a single infectious herpes simplex virus.

EXAMPLE 9

This example illustrates the use of the BHKICP6LacZ-5 cell line and the method of this invention to detect HSV-infected cells (and thus infectious HSV in a specimen) by fluorescence microscopy. The advantages of this assay are that it is very rapid (4 hours), very simple to perform, and the cells remain viable, thus allowing the same cells to be analyzed repeatedly over time.

A monolayer of approximately $2 \times 10^5$ BHKICP6LacZ-5 cells were grown in standard culture medium (MEM+10% fetal calf serum) on a commercially available tissue culture chambers/microscope slide device. The cells in individual chambers were inoculated with between 100 and 1000 pfu of HSV in 0.2 ml of medium, or mock infected with 0.2 ml of sterile medium, and then placed in a 37° C. incubator. In one hour intervals after infection the cells were processed in the following manner. The medium was aspirated and replaced with phosphate buffered saline (PBS) containing 4 mM FDG (fluorescein di-β-galactopyranoside, Molecular Probes, Eugene, Oreg.; cat. no. F-1179). FDG is a fluorogenic β-galactosidase substrate. After one minute at 37° C. the PBS/FDG was aspirated and fresh culture medium was added at ambient temperature. The cells were then observed immediately under an inverted microscope with a fluorescent light source (Zeis Axiovert 35) using the appropriate filters for fluorescein green fluorescence.

Mock infected (i.e., uninfected) cells displayed no visible fluorescence. Infected cells showed no fluorescence at 1 hour and 2 hours after infection. At 3 hours after infection, however, individual cells displayed a low level of fluorescence which increased to a dramatic level of fluorescence at 4 hours after infection. The number of fluorescence positive cells correlated with the number of pfu used in the infection. The fluorescence faded to a faint level over 30 minutes. The cells were placed back in a 37° C. incubator and were reassayed in exactly the same manner at 6, 12, and 16 hours after infection. The same number of fluorescence positive cells were seen at each time point from the 4 to 16 hours.

EXAMPLE 10

This example illustrates the preparation of the ICP10 promoter.

The ICP6 and ICP10 genes show a high degree of sequence homology particularly in the predicted amino acid sequences of the protein which they encode. The DNA sequences containing the promoters of these genes are upstream of the open reading frames of these genes and show a lesser degree of sequence homology. The ICP10 promoter was, therefore, prepared using polymerase chain reaction (PCR). The PCR primers were made based upon the published ICP10 promoter sequence of HSV-2 strain 333 as described in Wymer et al. (supra, 1989).

The DNA used as the template for the PCR reaction was obtained from Vero cells infected with HSV-2 (strain 333). $2 \times 10^6$ cells were infected with 0.05 plaque forming units (pfu) per cell ($10^5$ pfu). Three days after infection the media was removed. Viral DNA was isolated from a 100 microliter aliquot by extraction two times with phenol followed by two times with chloroform. The DNA was then precipitated with 2.5 volumes of 95% ethanol. The precipitate was dried and resuspended in 100 microliters of TE buffer (10 mM Tris, 1 mM EDTA, pH 8.0). One microliter was used in the PCR reaction.

Figure 7A:
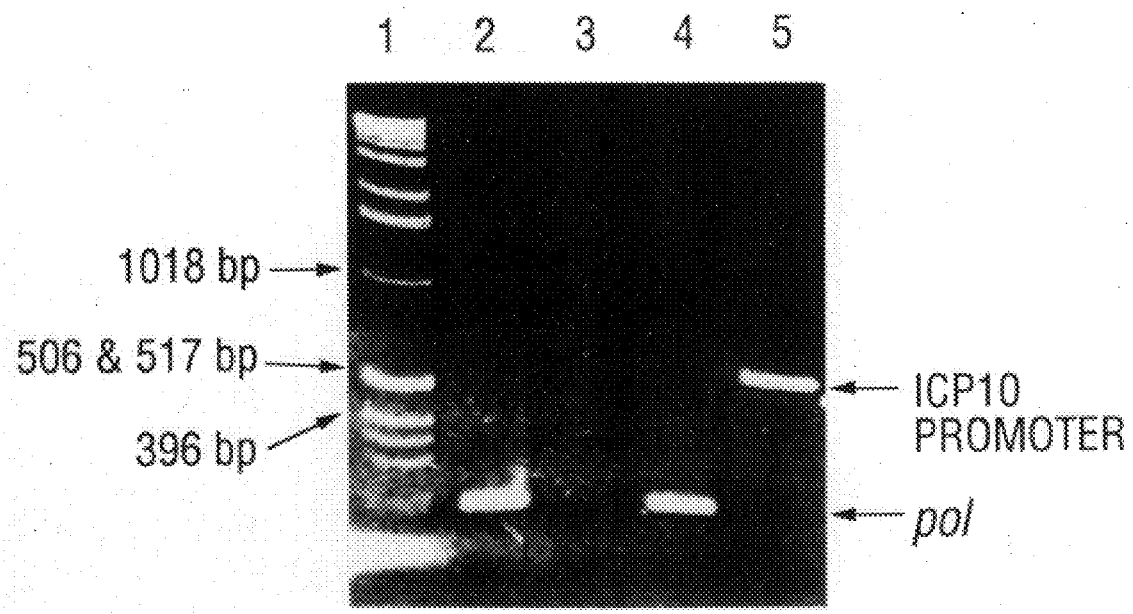
FIGS. 7A–7B illustrate (a) the ethidium bromide stained agarose gel electrophoresis of the ICP10 promoter PCR product using ICP10 promoter primers, 5'-GTCATGCCA GACAACAGC-3' (SEQ ID NO:1) and 5'-CCGACAGGAACGCAACAGG-3' SEQ ID NO:2); and (b) a schematic restriction map of the ICP10 PCR product.
Figure 7B:
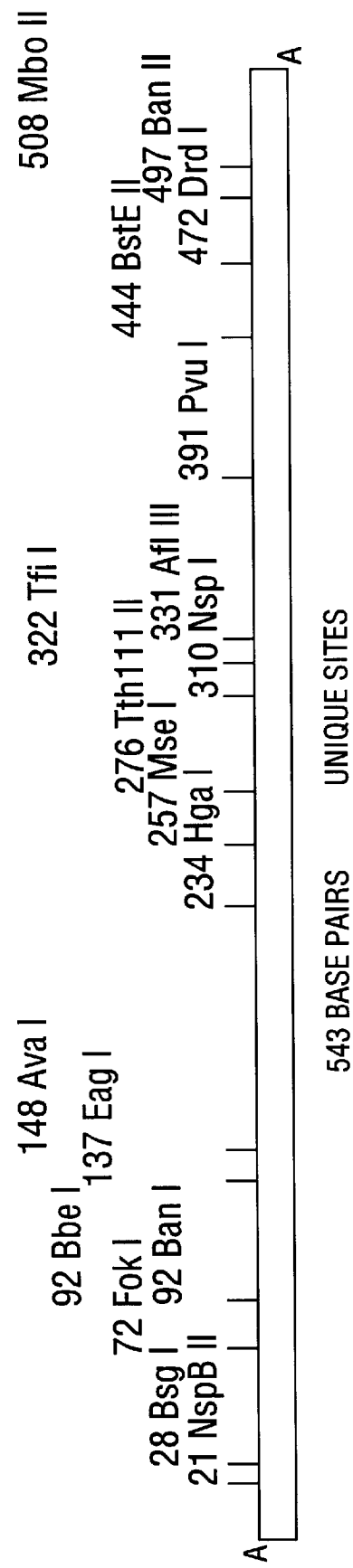

To amplify the ICP10 promoter of HSV-2, a PCR reaction was run with oligonucleotide primers based on the published sequence of the ICP10 promoter from HSV-2 strain 333 (see Wymer et al., 1989 and FIG. 7 therein).

The upstream (5') primer was 5'-GTCATGCCAGACAACAGC-3' (SEQ ID NO:1) and the downstream (3') primer was 5'-CCGACAGGAACGCAACAGG-3' (SEQ ID NO:2). Using these primers the predicted product would be a 543 bp fragment which extends from −448 to +94 relative to the start of transcription. Id.

PCR employed a Thermocycler 480 (Perkin Elmer Cetus, Norwalk, Conn.) using Taq DNA polymerase (Promega, Inc.) and standard techniques, well known in the art. See, for example Saiki, R. K. et al., *Science* 239:487–491 (1988).

The reaction mixture was distilled water, 82 μl; 10× PCR buffer, 10 μl; dNTP mix, 4 μl; primers, 1 μl each; DNA template, 1 μl; Taq DNA polymerase (5 u/μl), 0.5 μl. The samples were run under the following conditions denaturation at 95° C. for 1 minute, annealing at 58° C. for 1 minute, elongation at 72° C. for 1 minute for 35 cycles. Five microliters of the 100 microliter reaction were analyzed by electrophoresis in a 1% agarose gel followed by staining with ethidium bromide. Molecular weight markers were obtained from Gibco/BRL.

Using the ICP10 promoter primers and an HSV-2 (strain 333) DNA template, the PCR reaction amplified the 543 bp fragment. (see FIG. 7, lane 5). Three PCR reaction controls were additionally run. PCR amplification of the HSV-1 template DNA with pol primers resulted in the expected, pol PCR product (lane 2). The HSV-1 template DNA with ICP10 primers resulted in no product (lane 3). The HSV-2 DNA template with pol primers resulted in the pol product (lane 4). Thus, as expected, the pol primers did not discriminate between HSV-1 and HSV-2 and produced amplification products with both DNA templates. In contrast, the ICP10 promoter primers resulted in an amplification product with the HSV-2 DNA template only.

EXAMPLE 11

This example illustrates the cloning of the ICP10 promoter PCR product into the pGEM-T vector.

Figure 8:
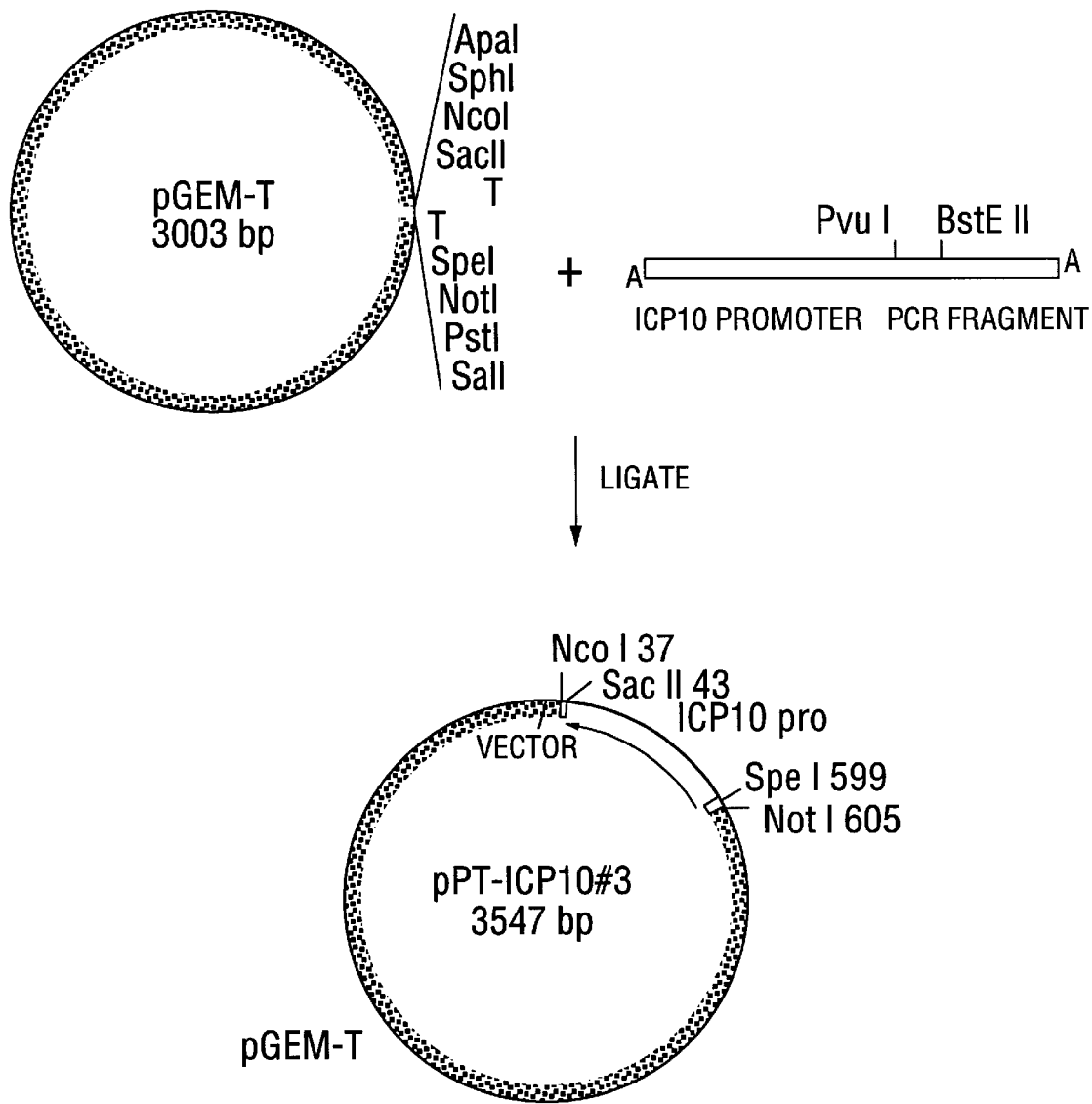
FIG. 8 is a schematic representation of the cloning of the ICP10 promoter PCR product into a pGEM-T vector.

The pGEM-T vector (obtained from Promega, Inc. Madison, Wis.) is a linear molecule with 3'-T overhangs to facilitate cloning of PCR products which have 3'-A ends added by the Taq DNA polymerase. One microgram of pGEM-T was ligated to the ICP10 promoter PCR product which was purified on a low melting temperature agarose gel. The ligation mixture was then used to transform E. coli (DH5a strain). Plasmid DNA was harvested from bacterial colonies which grew on ampicillin plates. To determine whether the plasmid DNA from each colony contained the ICP10 promoter fragment, each plasmid sample was analyzed by restriction enzyme digestion and agarose electrophoresis. For initial screening plasmids were digested with Pst I. There are no Pst I cleavage sites in pGEM-T and no sites in the 543 bp ICP10 promoter fragment. pGEM-T is 3003 bp and pGEM-T plus the ICP10 fragment is 3547 bp in length. Samples with 3547 bp fragments were selected for further analysis. The samples were digested with Nco I (in pGEM-T) and BstE II (in the ICP10 promoter fragment) (see FIG. 8). Because PCR fragments can be ligated to pGEM-T in either orientation the predicted products of a double digestion with Nco I and BstE II would be either 109 bp and 3438 bp or 459 bp and 3088 bp. Plasmids consistent with both orientations were represented among the samples and one of each orientation was saved and designated pPT-ICP10#1 and pPT-ICP10#3.

EXAMPLE 12

This example illustrates cloning the E. coli lacZ gene immediately downstream of the ICP10 promoter.

The vector, pPT-ICP10#3, was digested with Not I. The DNA ends were converted to 'blunt' ends with Klenow and 4 dNTPs according to well established protocols. The pPT-ICP10#3 sample was then digested with Nco I. This resulted in release of a 568 bp fragment which contained the ICP10 promoter containing an ATG initiation codon at its 3' end.

Another plasmid, pPOICP6LacZ was digested with Nco I and SnaB I. This resulted in two fragments: a 664 bp fragment and a 6028 bp fragment which contained both vector sequences and the lacZ gene with an Nco I site at its 5' end. The 6028 fragment and the 568 ICP10 promoter fragment were isolated and ligated together and the ligation reaction was used to transform E. coli. Ampicillin resistant colonies were isolated and plasmid DNA from ten colonies was harvested. The plasmids were then digested with Sac II which has one site in the ICP10 promoter and no sites in pPOICP6LacZ. All ten plasmids were linearized with Sac II resulting in a 6598 bp fragment consistent with the ICP10 promoter plasmid plus the 6028 lacZ containing vector. The plasmids were then digested with Sac II and Spe I which resulted in two fragments, a 6048 bp fragment and a 550 bp fragment, in all ten plasmid samples. This was consistent with the ICP10 promoter fragment being ligated to the lacZ gene. One plasmid sample was saved and designated pPTICP10LacZ. Further restriction enzyme digestions using Nco I, BstE II, and Pvu I were performed to verify that pPTICP10LacZ was as predicted.

Verification that the ICP10 promoter was operably linked to the lacZ gene was as follows: the vector pPTICP10LacZ was transfected into separate wells of BHK cells using lipofecin (Gibco/BRL) according to the manufacturer's suggestions. Forty-eight hours later the cells were superinfected with either HSV-1 or HSV-2, or mock infected. Sixteen hours later the cells were histochemically stained for β-galactosidase. Positive-stained cells were seen in both HSV-1 and HSV-2-infected wells but none were seen in the mock-infected wells. This result was consistent with transactivation of the ICP10 promoter by HSV.

EXAMPLE 13

This example illustrates the preparation of a susceptible cell line genetically engineered to enable it to detect infectious Herpes Simplex Virus.

Figure 9:
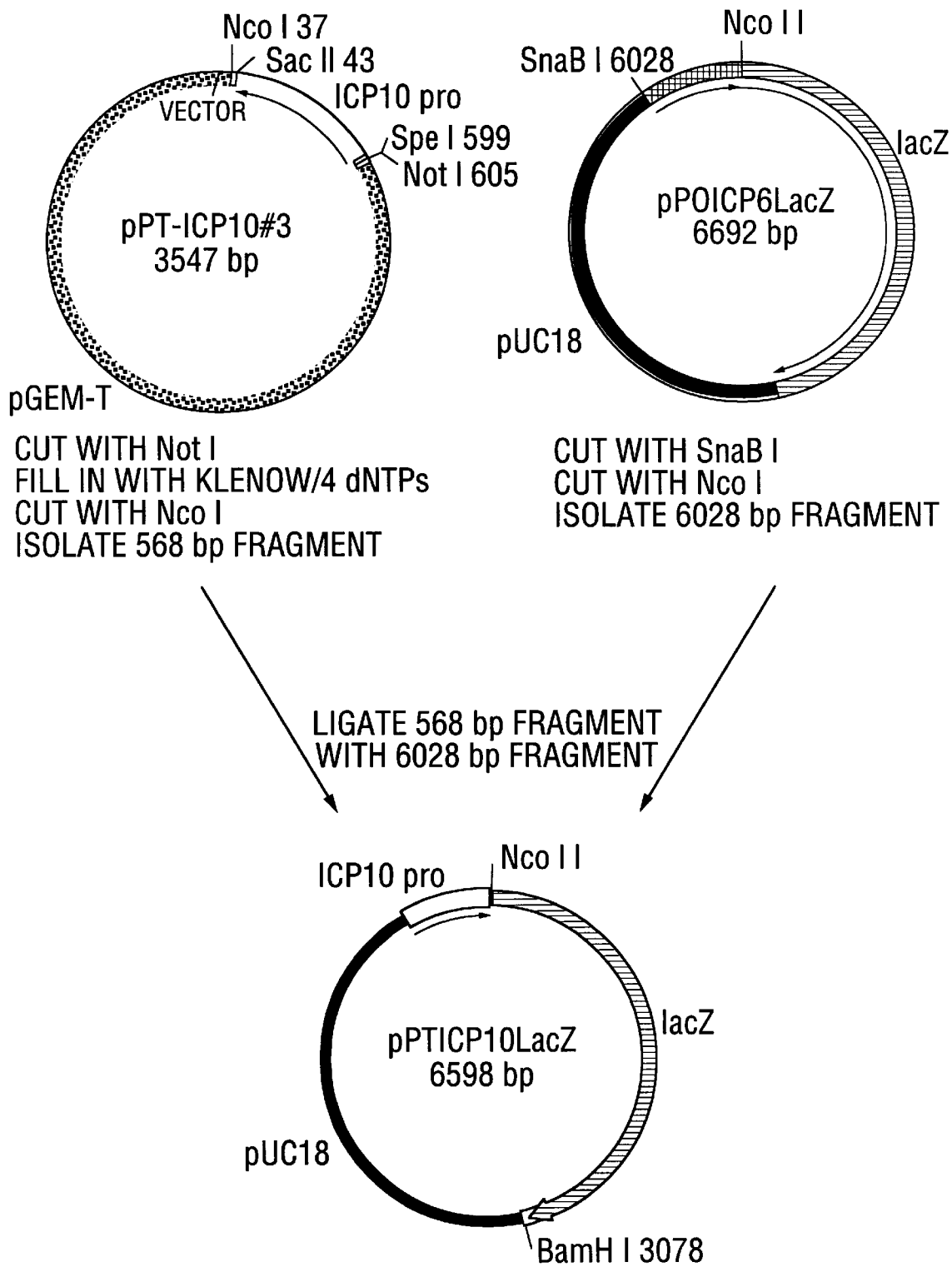
FIG. 9 is a schematic representation of the cloning of the *E. coli* lacZ gene immediately downstream of the ICP10 promoter.

Baby hamster kidney (BHK-21) cells were obtained from C. Hahn and C. Rice (Washington University, St. Louis, Mo.). The cells were propagated in MEM medium (Gibco-BRL, Gaithersburg, Md.) supplemented with 7% fetal calf serum (Gibco). Plasmid pPTICP10LacZ containing HSV-2 ICP10 and lacZ were mixed with PMamNeo, which contains the neo gene in a 10 to 1 molar ration. These plasmids were then co-transfected into BHK-21 cells by the liposomal transfection protocol as described in Maniatis, T., et al. (Molecular Cloning: A Laboratory Manual, Cold Spring Harbor Laboratory, 1990 which is incorporated by reference) using reagents obtained from Gibco-BRL. The essential features of plasmid pPTICP10LacZ are shown in FIG. 9. The plasmid pPTICP10LacZ was prepared according to Example 12. Plasmid pMAMneo contains the SV40 early promoter-Neomycin resistance gene cassette and was purchased commercially from Clontec, Palo Alto, Calif.

Twenty four hours after transfection, the cells were placed in selective medium containing 1 mg/ml G418 (Geneticin, Gibco: 50–60% active drug). The medium was changed daily for 4 days at which time the vast majority of the cells were killed. The cells were trypsinized and plated in 100 mm dishes in selective media. The media were changed every other day for one week and every fours days thereafter.

Following 1 to 2 weeks, the colonies that had formed were picked using a sterile trypsin/EDTA soaked cotton tip applicator and transferred to a 35 mm dish and grown in media containing 400 mg/ml G418. At least twenty separate clones were evaluated for HSV inducible β-gal activity. This initial screening was done by staining cell monolayers histochemically for β-gal activity following mock infection or infection with a laboratory strain of HSV-1 (KOS) or HSV-2 (strain 333). Those clones with high β-gal activity after infection were frozen for storage. One promising cell line, BHKICP10LacZ-17 (identified hereinafter as BHKICP10LacZ), displayed no detectable β-galactosidase activity after mock infection and pronounced activity following infection with HSV. This cell line was selected for further studies.

EXAMPLE 14

This example illustrates the ability of the BHKICP10LacZ to detect infectious herpes simplex virus in a specimen.

Cells from cell line BHKICP10LacZ as described in Example 12 were infected with HSV-1 OR HSV-2 at various multiplicities of infection (m.o.i.) in standard tissue culture medium. The cells and the virus were allowed to remain in culture for up to 12 hours after which the cells were assayed for β-galactosidase activity by the histochemical staining method in EXAMPLE 2.

Both HSV-1 and HSV-2 induced β-galactosidase activity that was demonstrable by 6 hours after infection. Control cells subject to no infection and mock infection exhibited no blue staining of the cells. Thus, the ICP10 promoter transfected into the cell line of this invention displays no constitutive expression and is transactivated on infection with HSV.

EXAMPLE 15

This example illustrates the specificity of BHKICP10LacZ cells in detecting only the presence of HSV in a specimen.

The specificity of the BHKICP10LacZ cells was determined according to the method in EXAMPLE 5. Monolayers of BHKICP10LacZ cells were inoculated, separately, with specimens known to contain other viruses and assayed histochemically for β-galactosidase activity. No β-galactosidase expression occurred 18 hours after infection of BHKICP10LacZ cells with each of four different viruses: varicella zoster virus, human cytomegalovirus, adenovirus type 5 and Sindbis virus. HSV-1 infection of BHKICP10LacZ cells resulted in β-galactosidase activity in a manner indistinguishable from HSV-2. Thus a cell line transfected with the ICP10 promoter and reporter gene as well as the method utilizing this cell line are specific for HSV-1 and HSV-2 (collectively HSV).

EXAMPLE 16

This example illustrates the stability of the transfected cell line BHKICP10LacZ.

The stability of BHKICP10LacZ cells was demonstrated by six passages in the absence of G418 selective pressure after which time the β-galactosidase activity was still inducible by HSV.

Genotypic analysis using PCR techniques confirmed the identity and stability of the BHKICP10LacZ cell line. Total cellular DNA was extracted from BHKICP10LacZ cells passed in the absence of selective pressure (i.e., without G418) and also from parental BHK cells. Using 5' primers homologous to the HSV-2 ICP10 promoter and 3' primers homologous to the lacZ open reading frame, a 500 bp fragment was amplified from the BHKICP10LacZ cells but not from the BHK cells. This demonstrated that the ICP10 promoter and the lacZ gene remained contiguous and that the BHKICP10LacZ cells are stably transformed with the ICP10 promoter:lacZ chimeric gene.

EXAMPLE 17

This example illustrates that the use of mixed cell cultures permits the detection and discrimination between HSV-1 and HSV-2. Mixed cell monolayers comprising a mixture of genetically engineered cells which contain DNA sequences comprising an HVS promoter linked to a reporter gene (e.g., the BHKICP6LacZ cell line) and a second cell line which is permissive for HSV infection [e.g., the MRC-5 cell line (ATCC CCL 171). The generation of the BHKICP6LacZ cell line is described in Example 1. The BHKICP6LacZ cell line is commercially available under the trade name ELVIS™ HSV Cells (Diagnostic Hybrids).

Infection of these mixed cell cultures (or mixed cell monolayers) with HSV-1 and HSV-2 followed by staining for β-galactosidase activity revealed that the distinct staining patterns were observed when the mixed monolayers were infected with these two types of HSV. Therefore, the use of mixed monolayer cultures permits the not only the detection of infectious HSV in a specimen but also permits the identification of the type, HSV-1 or HSV-2, of virus present in the specimen (i.e., permits typing of the specimen). The assays of the present invention, in contrast to existing assays which employ HSV type-specific monoclonal antibodies for the identification of the type of HSV present in a specimen (i.e., typing), does not require that duplicate cultures (or multiple sets of duplicate cultures) be infected with each specimen. This provides a considerable savings both in terms of cost and time.

a) Formation Of Mixed Cell Monolayers
In Multiwell Plates

Monolayers comprising a mixture of BHKICP6LacZ cells and MRC-5 cells were generated by plating or "seeding" BHKICP6LacZ cells onto a confluent monolayer of MRC-5 cells as described below.

i) Plating Of The MRC-5 Monolayer

MRC-5 cells were grown in Eagle's Minimal Essential Medium (EMEM) containing 10% FBS in T-225 tissue culture flasks (referred to as production flasks) (Costar) until confluent. The confluent cells were harvested from the flasks by trypsinization and suspended in EMEM containing 10% FCS. The concentration of the suspension was adjusted to a density of $3.75 \times 10^4$ cells/ml based on hemacytometer (Baxter, Deerfield, Ill.) or optical density determinations (1 $OD_{500} = 3.73 \times 10^6$ MRC-5 cells/ml).

One milliliter of the adjusted planting suspension was dispensed per well of a 24 well plate (Becton-Dickinson, Bridgewater, N.J.). The plates were then transferred to a 35° C. to 37° C. incubator, 5% $CO_2$ for a sufficient time for the MRC-5 cells to achieve confluence. Typically, the incubation period was three days.

ii) Plating Of ELVIS™ HSV Cells Onto The MRC-5 Monolayer

BHKICP6LacZ cells (hereinafter, ELVIS™ HSV cells; Diagnostic Hybrids) were grown in MEM medium containing 7% FBS in T-225 flasks until confluent. The cells were then harvested from the production flasks by trypsinization and suspended in fresh EMEM containing 7% FBS. The concentration of the cell suspension was adjusted to a density of $1.6 \times 10^4$ cells/ml based on hemacytometer (Baxter, Deerfield, Ill.) or optical density determinations (1 $OD_{500}=2.8 \times 10^6$ ELVIS™ HSV cells/ml).

The ELVIS™ HSV cell suspension was seeded onto confluent MRC-5 monolayers as follows. The original medium from wells containing the MRC-5 monolayers (24 well plates) was discarded and 1 ml of the ELVIS™ HSV cell suspension was added per well. The resulting monolayer contained approximately 90% MRC-5 cells and 10% ELVIS™ HSV cells. The plates were then transferred to a 35° C. to 37° C. incubator (humidified, 5% $CO_2$) for 16–24 hours.

b) Infection Of The Mixed Cell Monolayers

HSV-1 (Dr. W. T. Blue, Ohio University, Athens, Ohio) and HSV-2 (Dr. E. M. Swierkosz, St. Louis University, St. Louis, Mo.) viral stocks were diluted in EMEM with 7% FCS. Two-tenths of a ml of the appropriate dilution of virus (HSV-1 and HSV-2) required to yield MOIs of between 1 and $10^{-6}$ in 10-fold serial dilutions were used to inoculate the wells of 24-well multiwell plates. As used herein, an MOI of 1 typically indicates that every cell in the monolayer was infected, while an MOI of 0.001 indicates that only 1 in 1000 cells in the monolayer was infected.

The plates were then centrifuged at 700 g for 1 hour at room temperature in a Sorvall RT 6000D centrifuge (DuPont Medical Products, Hoffman Estates, Ill.). The plates were incubated at 37° C. in a humidified, 5% $CO_2$ incubator for 24 hours to allow for virus proliferation.

c) Fixation, Staining and Analysis Of The Infected Mixed Cell Monolayers

Figure 11A:
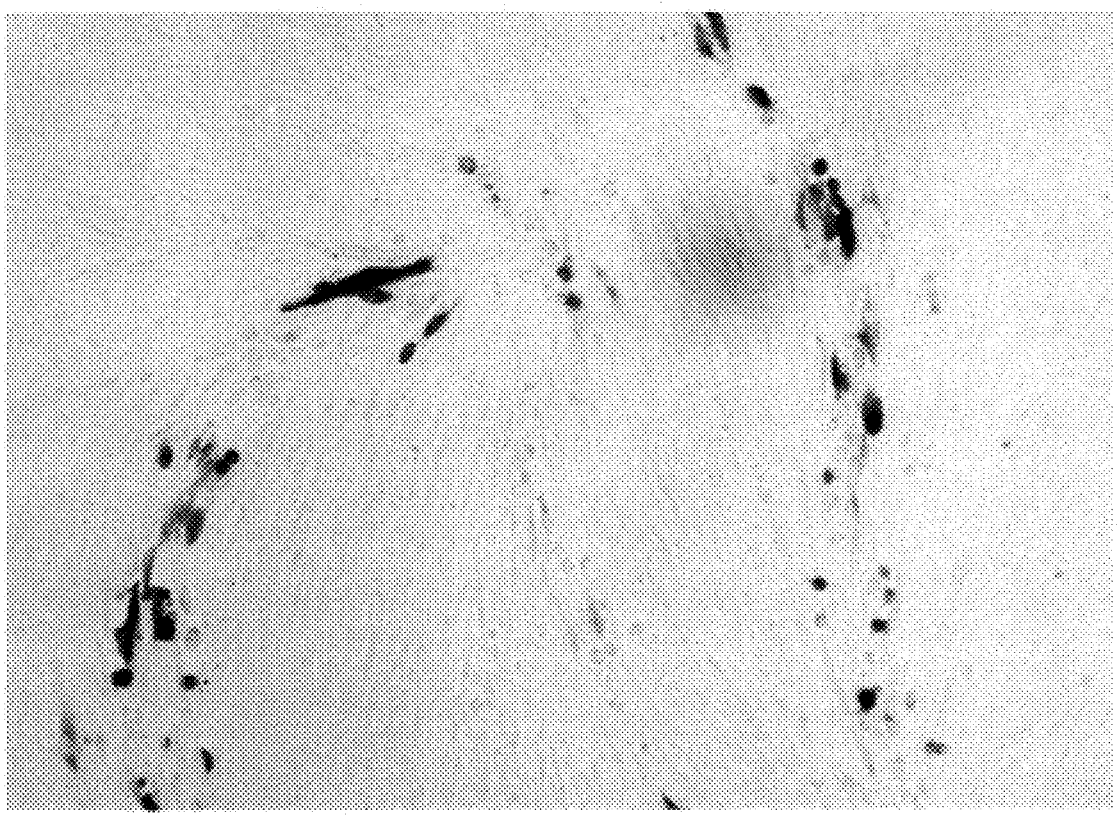
FIGS. 11A–11B are photographs of BHKICP10LacZ cell/ MRC-5 cell mixed cell monolayers infected with moderate levels of either HSV1 (Panel A) or HSV2 (Panel B) stained for β-galactosidase activity.
Figure 11B:
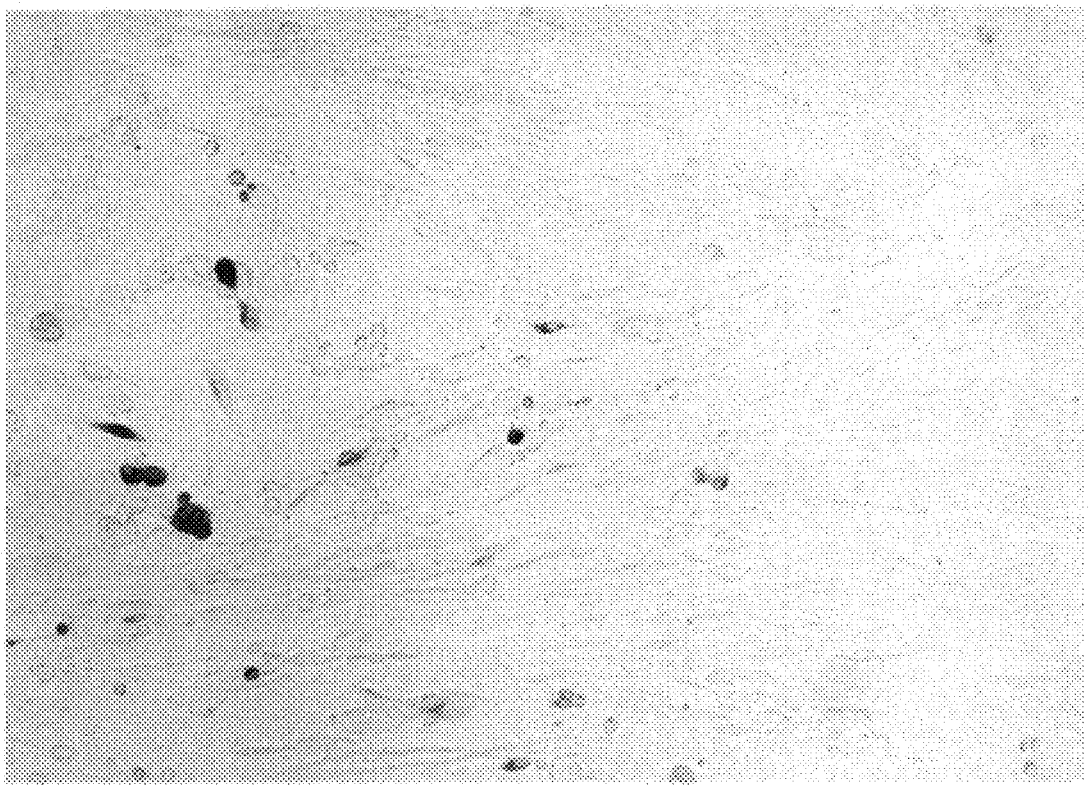
Figure 12A:
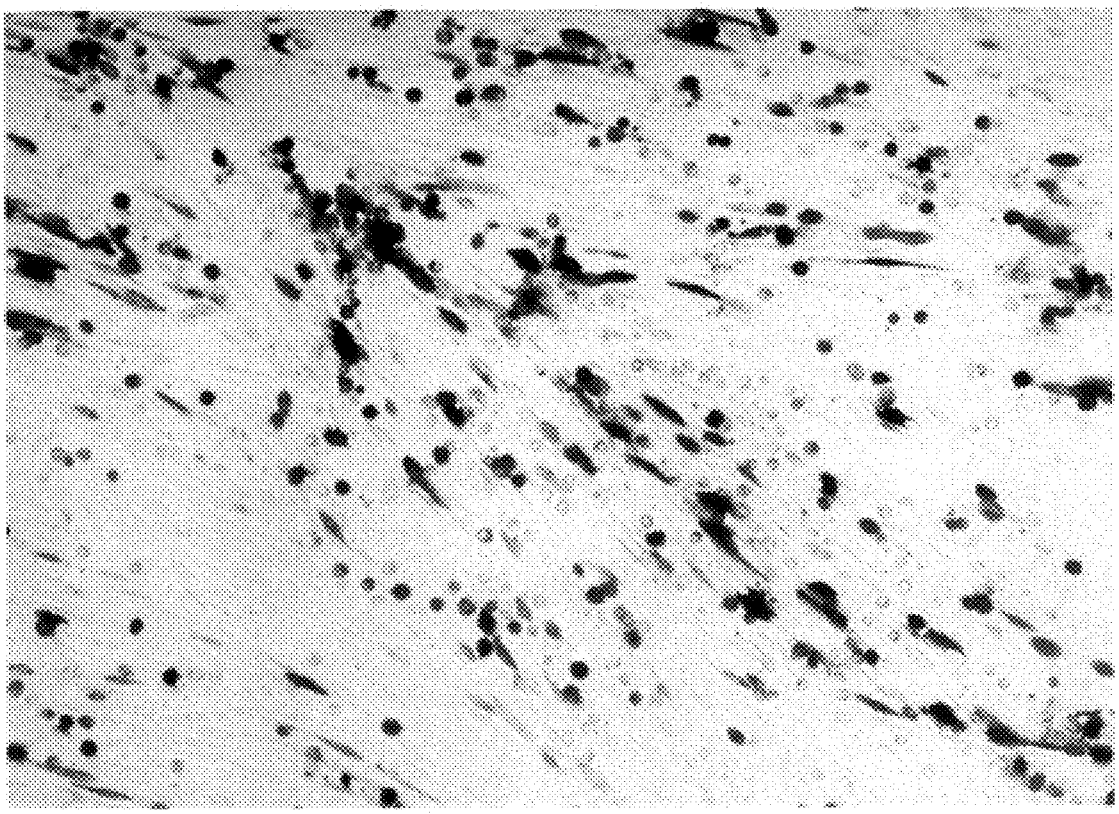
FIGS. 12A–12B are photographs of BHKICP10LacZ cell/MRC-5 cell mixed cell monolayers infected with high levels of either HSV1 (Panel A) or HSV2 (Panel B) stained for β-galactosidase activity.
Figure 12B:
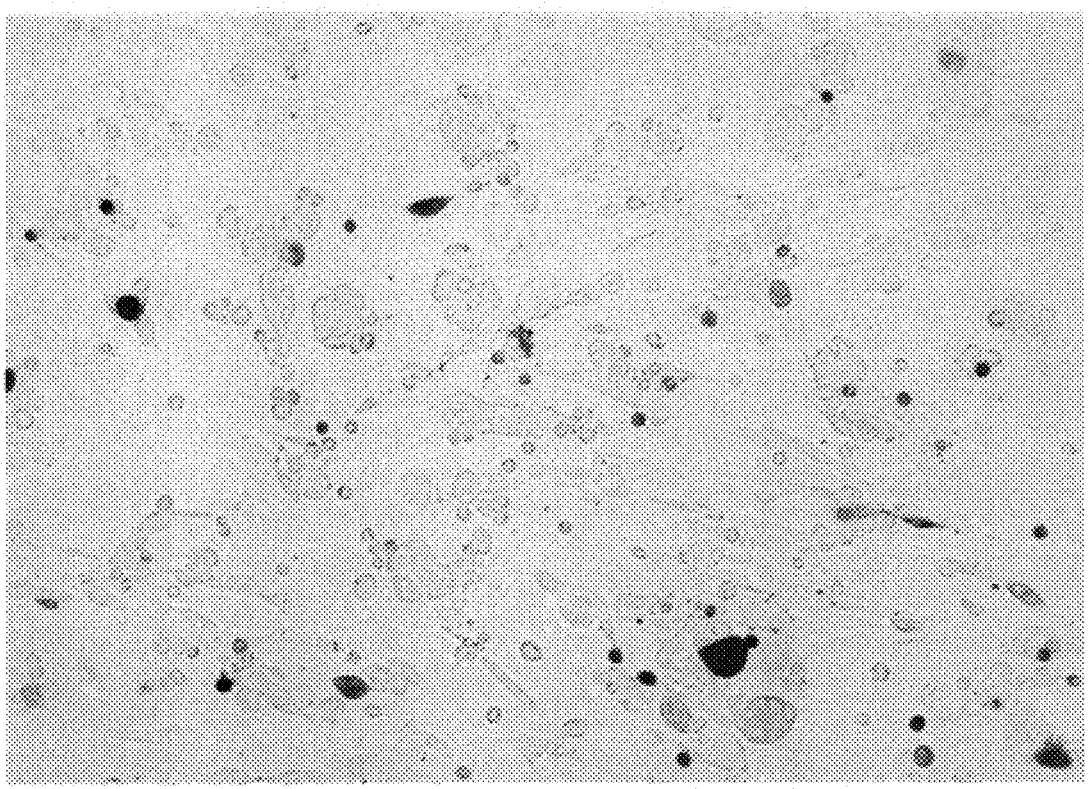

After incubation, the culture medium was discarded and the cells were fixed for 5 minutes with 0.5 ml 70% acetone in water (v/v), and the fixative solution discarded. The cells were stained with 0.5 ml X-gal staining buffer (#SK-ELVIS™ -100, Diagnostic Hybrids) for a period of 1–5 hours at 35° C. FIGS. 10–12 are photographs of mixed cell monolayers which depict representative staining patterns observed when the mixed monolayers were infected with either HSV-1 or HSV-2. The presence of blue color indicates the presence of a cell expressing the E. coli lacZ gene (i.e., β-galactosidase+ cells).

In FIG. 10, Panel A shows the results obtained when the mixed cell monolayer was infected with a low amount of HSV-1 at an MOI of $4 \times 10^{-5}$ and Panel B the results obtained when the mixed cell monolayer was infected with low levels of HSV-2 (MOI=$4 \times 10^{-5}$). In FIG. 11, Panel A shows the results obtained when the mixed cell monolayer was infected with moderate levels of HSV-1 (MOI=$4 \times 10^{-3}$); Panel B shows the results obtained when the mixed cell monolayer was infected with moderate levels of HSV-2 (MOI=$4 \times 10^{-3}$). In FIG. 12, Panel A shows the results obtained when the mixed cell monolayer was infected with high levels of HSV-1 (MOI=$4 \times 10^{-1}$); Panel B shows the results obtained when the mixed cell monolayer was infected with a low amount of HSV-2 (MOI=$4 \times 10^{-1}$). As is apparent from the results shown in FIGS. 10–12, distinct patterns of staining were observed, depending upon whether the mixed cell monolayer was infected with HSV-1 or HSV-2. A summary of the differences between the staining patterns observed in HSV-1 virus HSV-2 infected cells is provided in Table II. The HSV-type specific staining patterns and characteristic morphologies were seen in monolayers showing from 4+CPE down to a single small focus of infection. The photos shown in FIGS. 10–12 are from plate cultures of the mixed cell monolayers. However, the mixed cell monolayers formed in both tubes and shell vials presented the same typing characteristics.

TABLE II

|  | HSV-1 | HSV-2 |
| --- | --- | --- |
| 1. Distribution patterns of blue stained cells. | Swirling, uniform dense staining pre-dominate. | Irregular, dispersed pale to dense staining. |
| 2. Morphologic and color variation of affected areas of the monolayer. | Small rounded, uniform fibroid, no syncytia. | Large, multinucleate, many pale blue-green often unstained syncytia. |

All six high titer stock isolates were correctly identified as to HSV type at all levels of viral infectivity from an MOI of $4 \times 10^{-5}$ to an MOI greater than 1 at 24 hours post-infection using the microscopic criteria of Table II.

Figure 10A:
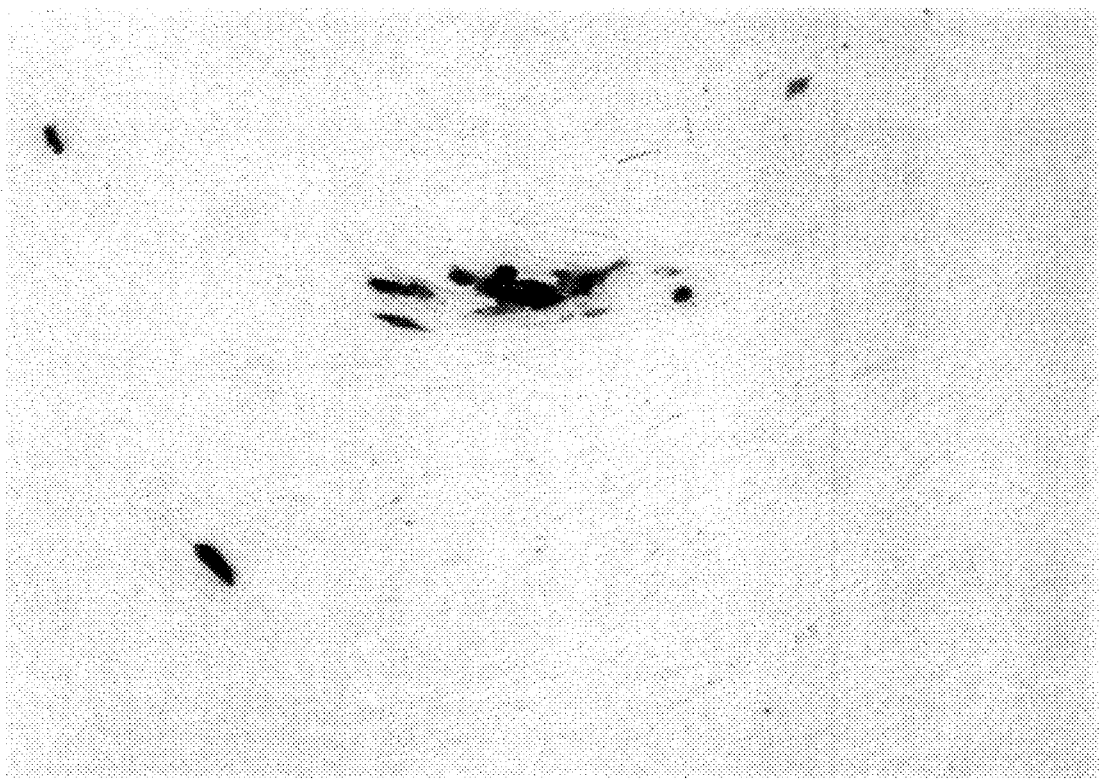
FIGS. 10A–10B are photographs of BHKICP10LacZ cell/MRC-5 cell mixed cell monolayers infected with low levels of either HSV1 (Panel A) or HSV2 (Panel B) stained for β-galactosidase activity.
Figure 10B:
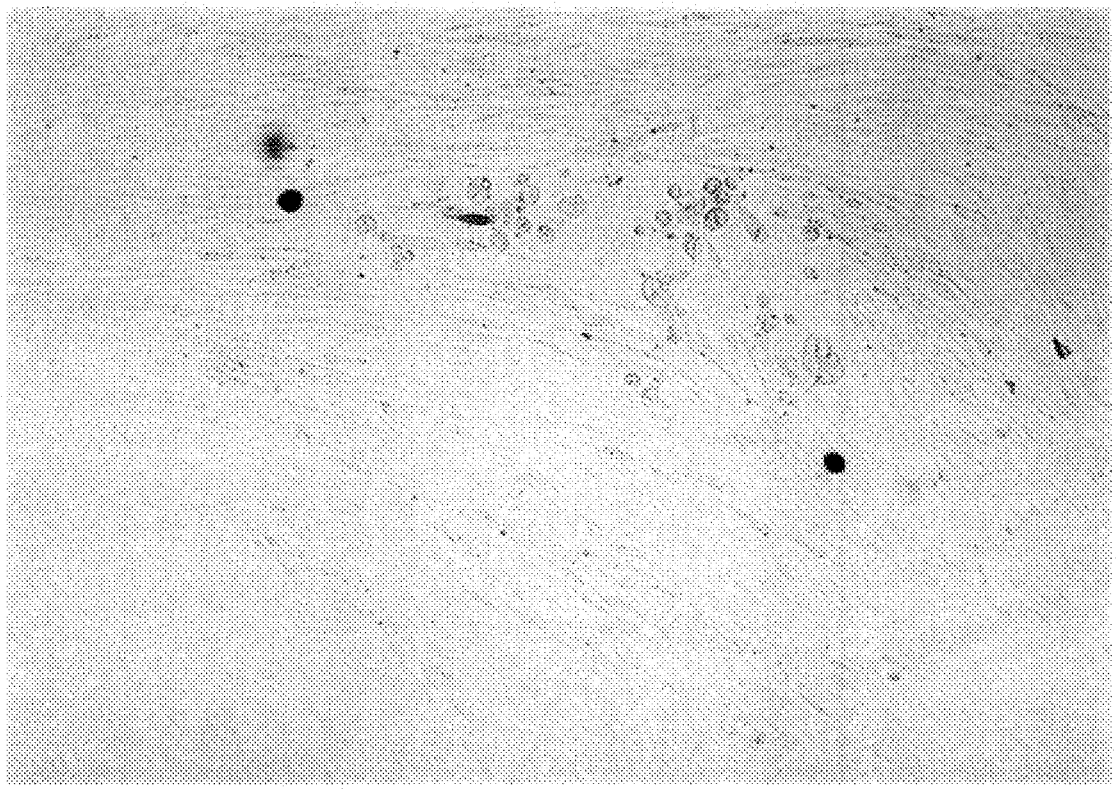

The photos shown in FIGS. 10A and B show, even at low titers, the characteristic staining, and cell patterns produced by infection of the mixed cell monolayer with the two types of HSV. FIG. 10A demonstrates the characteristic uniform dense staining obtained with HSV1 infection, in addition the cells are small, rounded with no syncytia present. In contrast, FIG. 10B demonstrates that the mixed cell monolayer shows a number of syncytia and large patches of dispersed pale to dense staining which are characteristic of infection with HSV2. These distinctive staining and cell morphological characteristics become even more evident at the higher titer levels reflected in FIGS. 11 and 12. The difference in color intensity between the two HSV types is also qualitatively demonstrated in Example 18 below.

EXAMPLE 18

This example illustrates the determination of β-galactoside activity in mixed cell monolayers infected with HSV type 1 and 2.

Mixed cell monolayers were prepared in 24 well multiwell plates (Diagnostic Hybrids) as described in Example 17. The monolayer cultures were inoculated with HSV1 or HSV2 at 500 plaque forming units (pfu) per well in 8 replicates. The plates were centrifuged at 700 g for 1 hour at room temperature then incubated at 37° C., 5% $CO_2$ for 24 hours. Following incubation, the medium was aspirated and lysates were prepared from each well by the addition of 1 ml 0.3% deoxycholate solution (Sigma)/well. Each lysate was thoroughly mixed and 100 μl of each lysate was added to each of 3 wells in a 96 well microtiter plate (Becton-Dickinson). β-galactoside activity was determined using colorimetric measurement of O-Nitrophenyl-β-D-Galactopyranoside (ONPG) (Sigma) hydrolysis as follows: seventy μl of ONPG substrate solution (Diagnostic Hybrids) was added to each well and the plates were incubated at room temperature for 45 minutes and then placed in the plate reader (Model EL309, Bio-tek Instruments, Inc. Wonooski, Vt.) and read at 405 nanometers. Lysates prepared were also prepared from uninfected wells and served as negative controls to provide background values. $OD_{405}$ readings from the 3 wells tested per sample were averaged and then divided by input virus numbers to give a value of OD/plaque forming unit. This allowed a comparison of β-galactosidase activity in the HSV-1 and HSV-2 infected wells to be made. The results are summarized in Table III below.

TABLE III

β-galactosidase Activity In HSV-1 And HSV-2 Infected Mixed Cell Monolayers As Measured By ONPG Hydrolysis[1]

| Promoter/Reporter | $OD_{405}$/pfu × $10^{-3}$ | | % Activity HSV-2 |
| --- | --- | --- | --- |
| | HSV-1 | HSV-2 | (HSV-1 = 100%) |
| ICP6/LacZ | 0.209 | 0.019 | 8.99 |
| ICP10/LacZ | 0.049 | 0.008 | — |

[1]The ICP6 data presented here was recorded at 45 minutes in the ONPG assay, while the ICP10 data were recorded after 135 minutes after incubation. The ICP10 values were so low (especially for HSV2 infection) that meaningful calculations could not be made. Because the ICP10 cell line produces less β-galactosidase per infected unit per unit time as compared to the ICP6 cell line, the data shown are not meant for cell line comparisons, rather they are presented to illustrate the difference in β-galactosidase activity between HSV-1 and 2 infected cells, regardless of the promoter controlling the reporter gene.

The results shown in Table III demonstrate that regardless of the origin of the promotor controlling the expression of the reporter gene, β-galactosidase activity is reduced in those cells infected with HSV-2 as compared to those infected with HSV-1 and consequently the color reaction resulting from the interaction of X-gal with β-gal is much more intense for cells infected with HSV-1 as compared to HSV-2.

EXAMPLE 19

This example illustrates the typing of clinical specimens using the mixed cell monolayer system of the present invention.

Fifty-six frozen clinical specimens were obtained from the Ohio Department of Health, Columbus, Ohio (ODC) and Indiana University Hospitals, Indianapolis, Ind. (IUH). These specimens had previously been or were concurrently typed using a fluorescent antibody assay (Syva MicroTrak® $HSV_1/HSV_2$ culture identification/typing test; Behring Diagnostic, San Jose, Calif.). These specimens were tested using the mixed monolayer cultures of the present invention as follows.

Mixed cell monolayers were prepared in the 24 multiwell plates according to the protocol of Example 17 below with the exception that they were prepared using a ratio of 10:90 BHKICP6LacZ cells: MRC5 cells. Wells were inoculated in duplicate with 0.2 ml of each thawed specimen, the plates centrifuged at 700 g at room temperature for 1 hour and the plates were then incubated at 37° C., 5% $CO_2$ for 24 hours. The medium was aspirated from the wells and the monolayers were fixed with 70% acetone (Sigma) for 1 minute. The fixative was aspirated and the monolayers covered with 0.3 ml of ELVIS™ Solution 2 containing X-Gal (lot SK-ELVIS-100; Diagnostic Hybrids). Monolayers were examined microscopically at 1 and 5 hours post-staining and the HSV type was determined according to the criteria described in Example 17. The results are summarized in Table IV below; Table IV provides a comparison between the results achieved using the mixed cell monolayers of the present invention and the results obtained using a conventional fluorescent antibody assay which employs Fab fragments specific for either HSV1 or HSV2.

TABLE IV

Typing Of Clinical Specimens Using Two Different Assays

| Assay Employed → | | Fluorescent Antibody Assay | |
| --- | --- | --- | --- |
| ↓ | HSV Type Identified | HSV-1 | HSV-2 |
| ELVIS ™ MCA | HSV-1 | 29 | 0 |
| | HSV-2 | 0 | 27 |

MCA = Mixed Cell Assay.

The data summarized in Table IV show that the mixed monolayer typing results were in complete accordance with the typing results using the standard type specific fluorescent antibody test (which uses Fab fragments specific for either HSV1 or HSV2). This antibody assay is currently employed by clinical virology diagnostic laboratories. The mixed monolayer correctly identified 29 type 1 isolates and 27 type 2 isolates among the 56 specimens tested.

Typing was also performed simultaneously using small glass dram vials (referred to as "shell vials") (Diagnostic Hybrids) and culture tubes. Shell vials containing a mixed cell monolayer were prepared according to the protocol of Example 17, with the exception that a ratio of 10:90 was used. The shell vial cultures were processed in the same manner as the multiwell plate cultures with the exception that the vials were capped tightly following inoculation and incubated in a standard incubator (i.e., without $CO_2$) incubator for 24 hours. Fixation, staining for β-galactosidase activity and reading were done as described for the multiwell plates. Again, 100% concordance with the clinical Fab typing results was achieved.

HSV typing was conducted using tube cultures. The tube cultures were prepared using a 10:90 BHK/MRC5 mixed monolayer prepared as described in Example 19. The tube cultures differed from the shell vial and plate cultures in this Example, in that 0.2 ml of each specimen was added directly to the medium (ELVIS™ Gold Replacement Medium which contains EMEM with 7% FBS, and 10 units/ml penicillin, 10 μg/ml streptomycin, 5 μg/ml gentamicin and 1.2 μg/ml amphotericin B/ml; Difco) in the duplicate tubes and the tubes were tightly capped and placed in a tube rotator (Glass-Cole, Model 108) at 37° C. As with the standard tube cultures, the tubes were examined daily for cytopathic effects (CPE). Once CPE were observed, the medium was aspirated and the monolayers were fixed and stained for β-galactosidase activity in the tube. The monolayers were then examined for the characteristic staining pattern and type determined. Once again, the results obtained using tube cultures were in 100% accordance with results obtained using the Fab assay.

The above results demonstrate that HSV typing can be performed using the mixed cell cultures of the present invention in multiwell plates, shell vials and tubes. The methods of the present invention represent a major improvement in efficiency and cost effectiveness in that only a single culture need be inoculated with the clinical specimen to allow discrimination between HSV1 and HSV2 in the specimen. In contrast, the currently employed Fab assay requires that two cultures be inoculated with each specimen to be tested.

EXAMPLE 20

This example illustrates the preparation of BHKICP6LacZ/MRC-5 mixed cell monolayers in tube cultures.
a) Plating Of The MRC-5 Monolayer MRC-5 cells grown, harvested from production flasks and cell suspensions were generated as described in Example 17. The concentration of the suspension was adjusted to a density of $5\times10^4$ cells/ml.

Two milliliters of the adjusted planting suspension was dispensed to flat-sided 16×100 mm plastic tubes (Nunc). The tubes were then capped and transferred to a standard incubator (i.e., without $CO_2$) at 35° C. to 37° C. for a sufficient time for the MRC-5 cells to achieve confluence. Typically, incubation lasted for approximately 3 days.
b) Plating Of ELVIS™ HSV Cells Onto The MRC-5 Monolayer The BHKICP6LacZ cells (ELVIS ™ HSV Cells Lot #EBI-P6; Diagnostic Hybrids) were grown, harvested from production flasks and cell suspensions were prepared as described in Example 17. The concentration of the suspension was adjusted to a density of $3\times10^4$ cells/ml.

The medium was aspirated from the MRC-5 tube monolayers in the flat-sided 16×100 mm plastic tubes and 2 ml of the adjusted ELVIS™ HSV cell suspension was added per tube; this volume contains the equivalent of 10% of the MRC-5 cells comprising the monolayers. The tubes were capped and transferred to a 35 to 37° C. incubator (no $CO_2$) for 16–24 hours prior to inoculation with virus.

EXAMPLE 21

This example illustrates the evaluation of mixed cell monolayers containing 1–4% ELVIS™ HSV (Lot EXP 072295)/MRC-5 cell mixtures.

Tube cultures were prepared according to the method of Example 20 with the exception that the ratio of ELVIS™ HSV cells plated or "seeded on" to the MRC-5 monolayer was either 1%, 2%, 3% and 4% of the cells present in the mixed/monolayer. Each set of mixtures was inoculated (4 replicates/set) with HSV type 1 QA virus (Dr. William Blue, Ohio University, Athens, Ohio) ($4TCID_{50}$/tube) and incubated at 37° C. The tube cultures were fixed and stained using the protocol in Example 17. The results are summarized below in Table V.

TABLE V

| Set | Tube # | Day 1 | 2 | 3 | 4 | 5 | 6 | 7 |
|-----|--------|---|----|---|---|---|---|---|
| 1% | 1. | N | PB | | | | | |
| | 2. | N | PB | | | | | |
| | 3. | N | PB | | | | | |
| | 4. | N | PB | | | | | |
| | NC 5. | N | N | N | N | N | N | N |
| | NC 6. | N | N | N | N | N | N | N |
| 2% | 1. | N | PB | | | | | |
| | 2. | N | PB | | | | | |
| | 3. | N | PB | | | | | |
| | 4. | N | PB | | | | | |
| | NC 5. | N | N | N | N | N | N | N |
| | NC 6. | N | N | N | N | N | N | N |
| 3% | 1. | N | PB | | | | | |
| | 2. | N | PB | | | | | |
| | 3. | N | PB | | | | | |
| | 4. | N | N | PB | | | | |
| | NC 5. | N | N | N | N | N | N | N |
| | NC 6. | N | N | N | N | N | N | N |
| 4% | 1. | N | PB | | | | | |
| | 2. | N | PB | | | | | |
| | 3. | N | PB | | | | | |
| | 4. | N | PB | | | | | |
| | NC 5. | N | N | N | N | N | N | N |
| | NC 6. | N | N | N | N | N | N | N |

N = No CPE seen.
P = CPE seen, no blue cells.
PB = CPE seen, blue cells seen.
NC = Negative control.

When CPE was apparent in the mixed cultures comprising 1–4% ELVIS™ HSV cells, blue cells were detected. All four sets of tubes demonstrated uniform monolayers through the 7 day incubation period. That is, while CPE is apparent, the monolayer had not broken down and was intact. Although all positive tubes showed blue cells, the 1% and 2% tubes had areas of minimal CPE without blue cells, making it necessary to scan the entire monolayer. Thus, while the monolayer remained intact for a sufficient length of time to permit tube typing to be accomplished, the quality of reporter response was low due to the low numbers of reporter cells and the presence of HSV could not be confirmed as quickly and efficiently as desired as compared to higher percentages (i.e. greater than 4% of ELVIS™ cells in mixed cell monolayers).

EXAMPLE 22

This example illustrates the evaluation of 2–10% ELVIS™ HSV cell/MRC-5 cell mixtures.

Tubes containing ELVIS™ HSV Cell/MRC-5 cell mixtures were prepared according to the method of Example 20 except that mixture tubes of 2%, 4%, 6%, 8%, and 10% ELVIS™ HSV cells/MRC-5 cells were prepared. Each set of tubes was inoculated (6 replicates of each percentage) with HSV type 2 lot 712-2 (Dr. E. M. Swierkosz, St Louis University, St. Louis, Mo.) to give 30 $TCID_{50}$/tube. This higher level of virus inoculum was used to assure that all 6 tubes of a set were infected. The intention of this evaluation was to examine the tubes frequently through the first 24 hours to catch the earliest possible signs of CPE, once CPE was evident, the cells were stained for β-galactosidase activity by the procedure of Example 17. Day 1 staining was done 19 hours past inoculation. The results are summarized in Table VI.

TABLE VI

| Set | Tube # | Day 1 | 2 | 3 | 4 | 5 | 6 | 7 |
|-----|--------|---|---|---|---|---|---|---|
| 2% | 1. | PB (5 blue cells) | | | | | | |
| | 2. | N | PB (>10 blue cells) | | | | | |
| | 3. | N | PB (>10 blue cells) | | | | | |
| | 4. | P (no blue) | | | | | | |

TABLE VI-continued

| Set | Tube # | Day 1 | 2 | 3 | 4 | 5 | 6 | 7 |
|---|---|---|---|---|---|---|---|---|
| | 5. | PB (>10 blue cells) | | | | | | |
| | 6. | N | PB (>10 blue cells) | | | | | |
| 4% | 1. | PB (blue clls) | | | | | | |
| | 2. | N | PB (>10 blue cells) | | | | | |
| | 3. | N | PB (>10 blue cells) | | | | | |
| | 4. | PB (>10 blue cells) | | | | | | |
| | 5. | N | PB (>10 blue cells) | | | | | |
| | 6. | N | PB (>10 blue cells) | | | | | |
| 6% | 1. | PB (>10 blue cells) | | | | | | |
| | 2. | PB (>10 blue cells) | | | | | | |
| | 3. | PB (>10 blue cells) | | | | | | |
| | 4. | N | PB (>10 blue cells) | | | | | |
| | 5. | N | PB (>10 blue cells) | | | | | |
| | 6. | PB (>10 blue cells) | | | | | | |
| 8% | 1. | PB | | | | | | |
| | 2. | N | PB | | | | | |
| | 3. | N | PB (many blue cells) | | | | | |
| | 4. | N | PB | | | | | |
| | 5. | N | PB | | | | | |
| | 6. | PB | | | | | | |
| 10% | 1. | N | PB | | | | | |
| | 2. | PB | | | | | | |
| | 3. | N | PB (many blue cells) | | | | | |
| | 4. | N | N | PB | | | | |
| | 5. | N | PB | | | | | |
| | 6. | PB | | | | | | |

N = No CPE seen.
P = CPE, seen, no blue cells
BP = CPE seen, blue cells seen.

The above results demonstrate that as the ELVIS™ HSV cells percentages were increased, more blue cells were seen. In this example, CPE was identified early on. Foci when seen on day 1 (at 19 hours) had fewer than 25 cells involved. In the case of the 2% cell mixture, blue cells were relatively rare in these early foci. One tube (tube 4) of the 2% mixture did not have any blue cells on one day examination. Negative control tubes (uninoculated) monolayers appeared intact at the end of the 7 day incubation period. Thus, the percentages tested in this example proved more suitable to a tube typing assay for HSV. Top end percentage mixtures (e.g., 8% and 10%) provided a number of positive reporter cells so that HSV could be readily confirmed, while the monolayer remained intact for the 7 day period which permitted typing based on CPE and staining patterns.

EXAMPLE 23

This example illustrates the evaluation of 4% to 16% ELVIS™ HSV Cells/MRC-5 Cell mixtures.

Cell mixture tubes containing 4%, 6%, 8%, 10%, 12%, and 16% ELVIS™ HSV Cells/MRC-5 Cells were prepared according to the method of Example 20, except that the "seed on" density of ELVIS™ HSV Cells was increased. Six replicate tubes of each set were inoculated with HSV type 1 QA virus (4TCID$_{50}$/tube) (Dr. W. T. Blue, Ohio University, Athens, Ohio) and 6 replicates of each set were inoculated with HSV type 2 QA virus (3TCID$_{50}$/tube). Tubes were incubated at 37° C. and examined daily for CPE. Uninoculated tubes of each set were incubated as negative controls. The results are summarized in Tables VII and VII.

TABLE VII

HSV Type 1

| Set | Tube # | Day 1 | 2 | 3 | 4 | 5 | 6 | 7 |
|---|---|---|---|---|---|---|---|---|
| 4% | 1. | N | N | PB | | | | |
| | 2. | N | PB | | | | | |
| | 3. | N | PB | | | | | |
| | 4. | N | N | PB | | | | |
| | 5. | N | PB | | | | | |
| | 6. | N | PB | | | | | |
| 6% | 1. | N | PB | | | | | |
| | 2. | N | N | PB | | | | |
| | 3. | N | N | PB | | | | |
| | 4. | N | PB | | | | | |
| | 5. | N | PB | | | | | |
| | 6. | N | PB | | | | | |
| 8% | 1. | N | PB | | | | | |
| | 2. | N | PB | | | | | |
| | 3. | N | PB | | | | | |
| | 4. | N | N | PB | | | | |
| | 5. | N | N | N | PB | | | |
| | 6. | N | PB | | | | | |
| 10% | 1. | N | PB | | | | | |
| | 2. | N | PB | | | | | |
| | 3. | N | N | PB | | | | |
| | 4. | N | PB | | | | | |
| | 5. | N | PB | | | | | |
| | 6. | N | PB | | | | | |
| 12% | 1. | N | PB | | | | | |
| | 2. | N | N | PB | | | | |
| | 3. | N | N | PB | | | | |
| | 4. | N | N | PB | | | | |
| | 5. | N | PB | | | | | |
| 16% | 1. | N | PB | | | | | |
| | 2. | N | PB | | | | | |
| | 3. | N | N | PB | | | | |
| | 4. | N | PB | | | | | |
| | 5. | N | PB | | | | | |
| | 6. | N | N | PB | | | | |

N = No CPE seen.
P = CPE seen, no blue cells.
BP = CPE seen, blue cells seen.

TABLE VIII

HSV Type 2

| Set | Tube # | Day 1 | 2 | 3 | 4 | 5 | 6 | 7 |
|---|---|---|---|---|---|---|---|---|
| 4% | 1. | N | N | PB | | | | |
| | 2. | N | PB | | | | | |
| | 3. | N | N | PB | | | | |
| | 4. | N | PB | | | | | |
| | 5. | N | PB | | | | | |
| | 6. | N | N | PB | | | | |
| 6% | 1. | N | PB | | | | | |
| | 2. | N | N | PB | | | | |
| | 3. | N | N | N | PB | | | |
| | 4. | N | PB | | | | | |
| | 5. | N | N | N | N | N | N | N |
| | 6. | N | PB | | | | | |
| 8% | 1. | N | N | PB | | | | |
| | 2. | N | N | N | N | N | N | N |
| | 3. | N | N | PB | | | | |

TABLE VIII-continued

| | | HSV Type 2 | | | | | | |
|---|---|---|---|---|---|---|---|---|
| | | Day | | | | | | |
| Set | Tube # | 1 | 2 | 3 | 4 | 5 | 6 | 7 |
| | 4. | N | PB | | | | | |
| | 5. | N | N | N | N | N | N | N |
| | 6. | N | | | | | | |
| 10% | 1. | N | PB | | | | | |
| | 2. | N | N | PB | | | | |
| | 3. | N | N | PB | | | | |
| | 4. | N | N | PB | | | | |
| | 5. | N | PB | | | | | |
| | 6. | N | PB | | | | | |
| 12% | 1. | N | PB | | | | | |
| | 2. | N | PB | | | | | |
| | 3. | N | N | | | | | |
| | 4. | N | N | PB | | | | |
| | 5. | N | N | PB | N | N | N | N |
| | 6. | N | N | N | | | | |
| 16% | 1. | N | PB | | | | | |
| | 2. | N | PB | | | | | |
| | 3. | N | N | N | N | N | N | N |
| | 4. | N | N | PB | | | | |
| | 5. | N | PB | | | | | |
| | 6. | N | N | PB | | | | |

N = No CPE seen.
P = CPE seen, no blue cells.
BP = CPE seen, blue cells seen.

"Seed on" ELVIS™ HSV Cell mixtures of 4–16% all demonstrate blue cells when CPE was detected. Negative controls incubated for 7 days indicate that the 16% seed on begins to compromise the MRC-5 appearance of the monolayer. While not limiting the invention to any particular mechanism, it is thought that as the percentage composition of the engineered cell line increases, ELVIS™ cells begin to overgrow and dominate the monolayer, and the smooth MRC-5 finish diminishes. The appearance of the monolayer becomes less satisfactory at percentages greater than or equal to 16% of the engineered cell line (ELVIS™). Although the aesthetics of these high percentages are not as pleasing, it is still possible to type the virus.

The 10% "seed on" provides numerous blue cells when CPE is detected yet the monolayer at 7 days is acceptable. The 10 percent "seed on" provided significant detection of HSV, with an intact monolayer which permitted the best detection and distinguishing of the HSV1 and HSV2 types based on the criteria of Example 19.

EXAMPLE 24

This example illustrates the use of the mixed cell monolayers of the present invention in an antiviral susceptibility or antiviral drug screening assay. In this example, acyclovir is used as the drug, although any other antiviral compound may be used in the present assay system.

Mixed cell monolayers of a 10:90 ratio (10% ELVIS™ HSV/90% MRC-5) are prepared according to the method of Example 17 in a 24 well plate. Upon reaching confluence, typically involving three days of incubation, the cells are inoculated with HSV as described in Example 17.

Samples suspected of containing HSV are first diluted in EME through two serial 10-fold dilutions. Aliquots of 0.2 ml of the undiluted sample, and the two dilutions ($10^{-1}$ and $10^{-2}$) are each used to inoculate duplicate wells containing the mixed cell monolayer culture. The plate is incubated for 90 minutes in a 37° C., 5% $CO_2$ incubator. One ml of EMEM is added to each well of one set (i.e., a "set" is one well of the undiluted sample, and one well of each dilution). This set is the "no drug" control. To the other set of wells one ml of a 2.0 µg Acyclovir in EMEM solution is added. This set is the "test." The plate is incubated at for additional time period, typically 40 hours.

Following this incubation period, the medium is aspirated from each well and 0.3 ml of 70% acetone in water (Fisher Chemicals, Pittsburgh, Pa.) is added to each well. The plate is incubated at room temperature for one minute. The acetone solution is then aspirated and replaced with 0.3 ml of histochemical stain containing X-Gal (Gold Biotechnology, St. Louis, Mo.). The plates are then incubated for 5 hours at 37° C. The wells are examined microscopically (e.g., at 400× and 1000×) for the presence of cells that are stained blue.

Wells which contain blue-stained cells are counted as "positive" for infection with HSV. The presence of blue cells in the "no drug" control indicates that the specimen is HSV-positive. If the specimen is positive, the wells containing acyclovir are observed for the presence of blue-stained cells. The absence of blue cells in the test wells indicates that the HSV isolate is sensitive to the drug. The presence of blue-stained cells in the $10^{-1}$ dilution, but not the $10^{-2}$ dilution indicates that the HSV isolate is somewhat sensitive to the drug. The presence of blue-stained cells in both dilutions indicates that the HSV isolate is not sensitive to the drug. These wells should also be examined for CPE. Based on the results obtained, the virus present may be typed as HSV-1 or HSV-2.

EXAMPLE 25

This example illustrates the use of the mixed cell monolayers of the present invention in an in vitro neutralization screening assay for the presence or absence of antibodies proficient in neutralizing a particular virus in suspension.

Patient serum is diluted in Phosphate Buffered Saline (Sigma, St Louis, Mo.) through 10 serial 2-fold dilutions by adding 0.5 ml of the patient serum specimen to the first dilution tube containing 0.5 ml PBS. Label "1:2." Take 0.5 ml of the 1:2 dilution and add to 0.5 ml PBS in a second tube and label 1:4. Repeat the procedure 8 times. Transfer the undiluted serum specimen and each of the serial dilutions to 5 ml polystyrene screw cap tubes (Falcon) which contain 100 Pfu HSV-1 or HSV-2 in 0.01 ml EMEM and incubate for 1 hours at 37° C. Transfer the tube contents to 10:90 mixed cell monolayer wells prepared according to the method of Example 17 and add 1 ml EMEM to each well. Label the wells for the respective dilution. Inoculate two wells with 100 pfu of the virus in 1 ml EMEM to serve as positive controls and label as such. Incubate the inoculated plate for 24 hours in a 37° C., 5% $CO_2$. Aspirate the medium from each well and replaced with 0.3 ml of histochemical stain containing X-Gal (Gold Biotechnology, St Louis, Mo.). Incubate the plates at 37° C. for 5 hours. Examine wells microscopically at 40× and 100× magnification. Identify wells containing blue cells. Determine viral titer.

It is clear from the above examples that the present invention provides improved methods for the detection and typing of virus in specimens. Those skilled in the art know that various changes could be made in the above examples and methods without departing from the scope of the invention, it is intended that all matter contained in the above description shall be interpreted as illustrative and not in a limiting sense.

What is claimed is:

1. A method for the detection of infectious virus in a specimen comprising the steps of:
   a) providing:
      a specimen suspected of containing a virus;
      ii) a cell line permissive for infection by said virus;
      iii) a genetically engineered cell line susceptible to infection by said virus, said genetically engineered cell line containing a nucleic acid molecule having a sequence comprising a promoter sequence derived from said virus wherein said promoter sequence is operably linked to a reporter gene, the expression of said reporter gene being dependent upon and quantitatively proportional to the presence of said virus;
   b) mixing together said permissive cell line and said genetically engineered cell line to create a mixed cell culture;
   c) inoculating said mixed cell culture with said specimen under conditions which permit the infection of said mixed cell culture by said virus; and
   d) detecting the expression of said reporter gene and thereby detecting the presence of said virus in said specimen.

2. The method of claim 1 wherein said mixed cell culture is a mixture consisting of 80–99 percent of said permissive cell line and 1–20 percent of said genetically engineered cell line.

3. The method of claim 1 wherein said promoter sequence contains a promoter derived from a gene selected from the group consisting of genes that encode ribonucleotide reductase and genes that encode one or more subunits of ribonucleotide reductase.

4. The method of claim 1 wherein said genetically engineered cell line contains a nucleic acid molecule having a sequence comprising a herpesvirus inducible promoter operably linked to a reporter gene selected from the group consisting of the *Escherichia coli* lacZ gene and a luciferase gene.

5. The method of claim 1 wherein said genetically engineered cell line is selected from the group consisting of BHKICP10LacZ and BHKICP6LacZ.

6. The method of claim 1 wherein said permissive cell line is permissive for infection with herpesvirus.

7. The method of claim 3 wherein said promoter sequence is derived from a gene that encodes a large subunit of a ribonucleotide reductase and wherein said virus is a member of the herpesvirus family.

8. The method of claim 6 wherein said permissive cell line is MRC-5.

9. The method of claim 7 wherein the member of said herpesvirus family is selected from the group consisting of Herpes Simplex Virus Type 1, Herpes Simplex Virus Type 2, Human Cytomegalovirus, Varicella-Zoster Virus, Epstein-Barr Virus, Human Herpes Virus 6, Human Herpes Virus 7, and Human Herpes Virus 8.

10. The method of claim 9 wherein said promoter sequence is the ICP10 promoter and said herpesvirus is Herpes Simplex Virus Type 2.

11. The method of claim 9 wherein said promoter sequence is the ICP6 promoter and the herpesvirus is Herpes Simplex Virus Type 1.

12. A method for the detection of infectious herpesvirus in a specimen comprising the steps of:
  a) providing:
    i) a specimen suspected of containing a herpesvirus;
    ii) a cell line permissive for infection by said herpesvirus;
    iii) a genetically engineered cell line susceptible to infection by said herpesvirus, said genetically engineered cell line containing a nucleic acid molecule having a sequence comprising a herpesvirus inducible promoter sequence derived from said herpesvirus, wherein said promoter sequence is operably linked to a reporter gene, the expression of said reporter gene being dependent upon and quantitatively proportional to the presence of said herpesvirus and wherein said reporter gene is selected from the group consisting of *Escherichia coli* lacZ gene and a luciferase gene;
  b) mixing together said permissive cell line and said genetically engineered cell line to create mixed cell culture;
  c) inoculating said mixed cell culture with said specimen under conditions which permit the infection of said mixed cell culture by said herpesvirus; and
  d) detecting the expression of said reporter gene and thereby detecting the presence of said herpesvirus in said specimen.

13. The method of claim 12 wherein said mixed cell culture is a mixture consisting of 80–99 percent of said permissive cell line and 1–20 percent of said genetically engineered cell line.

14. The method of claim 12 wherein said promoter sequence contains a promoter derived from a gene selected from the group consisting of genes that encode ribonucleotide reductase and genes that encode one or more subunits of ribonucleotide reductase.

15. The method of claim 14 wherein said promoter sequence is derived from a gene that encodes a large subunit of a ribonucleotide reductase.

16. The method of claim 15 wherein said herpesvirus is selected from the group consisting of Herpes Simplex Virus Type 1, Herpes Simplex Virus Type 2, Human Cytomegalovirus, Varicella-Zoster Virus, Epstein-Barr Virus, Human Herpes Virus 6, Human Herpes Virus 7, and Human Herpes Virus 8.

17. The method of claim 16 wherein said promoter sequence is the ICP10 promoter and said herpesvirus is Herpes Simplex Virus Type 2.

18. The method of claim 16 wherein said promoter sequence is the ICP6 promoter and the herpesvirus is Herpes Simplex Virus Type 1.

19. A method for the detection of infectious virus in a specimen comprising the steps of:
  a) providing:
    i) a specimen suspected of containing a virus;
    ii) a cell line permissive for infection by said virus;
    iii) a genetically engineered cell line susceptible to infection by said virus, said genetically engineered cell line stably transformed with a nucleic acid molecule having a sequence comprising a promoter sequence derived from said virus wherein said promoter sequence is operably linked to a reporter gene, the expression of said reporter gene being dependent upon and quantitatively proportional to the presence of said virus;
  b) mixing together said permissive cell line and said genetically engineered cell line to create a mixed cell culture;
  c) inoculating said mixed cell culture with said specimen under conditions which permit the infection of said mixed cell culture by said virus; and
  d) detecting the expression of said reporter gene and thereby detecting the presence of said virus in said specimen.

20. The method of claim 19 wherein said mixed cell culture is a mixture consisting of 80–99 percent of said permissive cell line and 1–20 percent of said genetically engineered cell line.

21. The method of claim 19 wherein said promoter sequence contains a promoter derived from a gene selected from the group consisting of genes that encode ribonucleotide reductase and genes that encode one or more subunits of ribonucleotide reductase.

22. The method of claim 21 wherein said promoter sequence is derived from a gene that encodes a large subunit of a ribonucleotide reductase and wherein said virus is a member of the herpesvirus family.

23. The method of claim 22 wherein the member of said herpesvirus family is selected from the group consisting of Herpes Simplex Virus Type 1, Herpes Simplex Virus Type 2, Human Cytomegalovirus, Varicella-Zoster Virus, Epstein-Barr Virus, Human Herpes Virus 6, Human Herpes Virus 7, and Human Herpes Virus 8.

24. The method of claim 23 wherein said promoter sequence is the ICP10 promoter and said herpesvirus is Herpes Simplex Virus Type 2.

25. The method of claim 23 wherein said promoter sequence is the ICP6 promoter and the herpesvirus is Herpes Simplex Virus Type 1.

* * * * *

UNITED STATES PATENT AND TRADEMARK OFFICE
CERTIFICATE OF CORRECTION

PATENT NO. : 5,939,253
DATED : 08/17/99
INVENTOR(S) : David R. Scholl et al.

Page 1 of 4

It is certified that error appears in the above-identified patent and that said Letters Patent is hereby corrected as shown below:

In column 3, line 22, please delete "325:67 70;" and insert -- 325:67-70; --.
In column 4, line 53, please delete "adsorb" and insert -- adsorbed --.
In column 7, line 64, please delete "histochemically" and insert -- histochemical --.
In column 12, line 65, please delete "tk" and insert -- tk⁻ --.
In column 13, line 22, please insert -- as -- between "such" and "viruses."
In column 13, line 38, please delete "form" and insert -- from --.
In column 14, line 20, please delete "absorption" and insert -- adsorption --.
In column 16, line 30, please delete "absorption" and insert -- adsorption --.
In column 16, line 62, please delete "cell lines," and insert -- cell lines; --.
In column 16, line 63, please delete "(HEF)," and insert -- (HEF); --.
In column 16, line 64, please delete "cells," and insert -- cells; -- (both times).
In column 16, line 65, please delete "carcinoma)," and insert -- carcinoma); --.
In column 17, line 65, please delete "following" and insert -- Following --.
In column 19, line 11, please delete "HHV6 or HHV7," and insert -- HHV6, HHV7, or --.

UNITED STATES PATENT AND TRADEMARK OFFICE
CERTIFICATE OF CORRECTION

PATENT NO. : 5,939,253
DATED : 08/17/99
INVENTOR(S) : David R. Scholl et al.

It is certified that error appears in the above-identified patent and that said Letters Patent is hereby corrected as shown below:

In column 19, line 29, please delete "376 384" and insert -- 376 - 384 --.
In column 19, line 29, please delete "example," and insert -- example --.
In column 20, line 9, please delete "immediateearly" and insert -- immediate-early --.
In column 20, line 26, please delete "wellcharacterized" and insert -- well-characterized --.
In column 20, line 42, please delete "signal)or" and insert -- signal) or --.
In column 21, line 36, please delete "," after "typically".
In column 23, line 9, please delete "absorb" and insert -- adsorb --.
In column 23, line 25, please delete "whiich" and insert -- which --.
In column 23, line 33, please delete "anitiviral" and insert -- antiviral --.
In column 24, line 49, please delete "framne" and insert -- frame --.
In column 25, line 25, please delete "Elvis" and insert -- ELVIS™ --.
In column 25, line 43, please delete "DNTP" and insert -- dNTP --.
In column 25, line 54, please delete "ethylenediaminetetracetic" and insert -- ethylenediaminetetraacetic --.
In column 27, line 2, please delete "titre" and insert -- titer --.
In column 27, line 14, please delete "absorb" and insert -- adsorb --.

UNITED STATES PATENT AND TRADEMARK OFFICE
CERTIFICATE OF CORRECTION

PATENT NO. : 5,939,253
DATED : 08/17/99
INVENTOR(S) : David R. Scholl et al.

Page 3 of 4

It is certified that error appears in the above-identified patent and that said Letters Patent is hereby corrected as shown below:

In column 27, line 35, please delete "titre" and insert -- titer --.
In column 28, line 53, please delete "titre" and insert -- titer --.
In column 28, line 54, please delete "0.15" and insert -- 0.5 --.
In column 30, line 6, please delete "than" and insert -- that --.
In column 31, line 17, please delete "titre" and insert -- titer --.
In column 31, line 46, please delete "titre" and insert -- titer --.
In column 33, line 2, please delete "conditions" and insert -- conditions: --.
In column 40, line 38, please delete the first "incubator".
In column 41, line 44, please delete "and" and insert -- or --.
In column 43, Table VI caption, please delete "BP" and insert -- PB --.
In column 44, Table VII caption, please delete "BP" and insert -- PB --.
In column 45, Table VIII, in the 12% row, #3, please insert -- PB --.
In column 45, Table VIII caption, please delete "BP" and insert -- PB --.
In column 46, line 4, please delete "at" and insert, after the "for", -- an --.

UNITED STATES PATENT AND TRADEMARK OFFICE
CERTIFICATE OF CORRECTION

PATENT NO. : 5,939,253
DATED : 08/17/99
INVENTOR(S) : David R. Scholl et al.

It is certified that error appears in the above-identified patent and that said Letters Patent is hereby corrected as shown below:

In column 46, line 65, please delete "invention, it" and insert --invention. It --.

In column 47, line 45, please insert -- i) -- before "a specimen".

Signed and Sealed this

Third Day of October, 2000

Attest:

Q. TODD DICKINSON

*Attesting Officer*    *Director of Patents and Trademarks*